United States Patent [19]
Schieven

[11] Patent Number: 5,583,242
[45] Date of Patent: Dec. 10, 1996

[54] USE OF PHOSPHOTYROSINE PHOSPHATASE INHIBITORS FOR CONTROLLING CELLULAR PROLIFERATION

[75] Inventor: Gary L. Schieven, Seattle, Wash.

[73] Assignee: Bristol-Myers Squibb Company, New York, N.Y.

[21] Appl. No.: 450,342

[22] Filed: May 25, 1995

Related U.S. Application Data

[62] Division of Ser. No. 189,330, Jan. 31, 1994.

[51] Int. Cl.$^6$ ........................................................ C07F 5/00
[52] U.S. Cl. ............................... 556/44; 556/1; 556/42; 556/114; 556/116; 556/117
[58] Field of Search ................................... 556/1, 42, 44, 556/114, 116, 117

[56] References Cited

U.S. PATENT DOCUMENTS

| | | | |
|---|---|---|---|
| 5,023,358 | 6/1991 | Lazaro et al. | 556/42 |
| 5,175,001 | 12/1992 | Lazaro et al. | 424/451 |

OTHER PUBLICATIONS

G. J. V. Nossal, "Cellular Mechanisms of Immunologic Tolerance," *Annu. Rev. Immunol.* 1:33–62 (1983).
F. M. Uckun & J. A. Ledbetter, "Immunobiologic Differences Between Normal and Leukemic Human Cell Precursors," *Proc. Natl. Acad. Sci. USA* 85:8603–8607 (1988).
T. R. Burke et al., "Preparation of Fluoro—and Hydroxy-4-(Phosphonomethyl)-D,L-Phenylalanine Suitably Protected for Solid-Phase Synthesis of Peptides Containing Hydrolytically Stable Analogues of O-Phosphotyrosine," *J. Org. Chem.* 58:1336–1340 (1993).
D. B. A. de Bont et al., "Solid-Phase Synthesis of O-Phosphorothioylserine-and -Threonine-Containing Peptides as Well as of O-Phosphoserine- and -Threonine-Containing Peptides," *J. Org. Chem.* 58:1309–1317 (1993).
K. Guan et al., "A Tyr/Ser Protein Phosphatase Encoded by Vaccinia Virus," *Nature* 350:359–362 (1991).
D. Dailey et al., "Novel Yeast Protein Kinase (*YPK*1 Gene Product) Is A 40-Kilodalton Phosphotyrosyl Protein Associated with Protein–Tyrosine Kinase Activity," *Mol. Cell. Biol.* 10:6244–6256 (1990).
M. Imoto et al., "Dephostatin, a Novel Protein Tyrosine Phosphatase Inhibitor Produced by *Streptomyces*. I. Taxonomy, Isolation, and Characterization," *J. Antibiotics* 46:1342–1346 (1993).
J. H. McNeill et al., "Bis(maltolato)oxovanadium (IV) Is a Potent Insulin Mimic," *J. Med. Chem.* 35:1489–1491 (1992).
R. R. Bartlett et al., "Leflunomide (HWA 486), a Novel Immunomodulating Compound for the Treatment of Autoimmune Disorders and Reactions Leading to Transplantation Rejection," *Agents & Actions* 32:10–21 (1991).
J. K. Myers & T. S. Widlanski, "Mechanism-Based Inactivation of Prostatic Acid Phosphatase," *Science* 262:1451–1453 (1993).

L. B. Justement et al., "Regulation of B Cell Antigen Receptor Signal Transduction and Phosphorylation by CD45," *Science* 252:1839–1842 (1991).
M. R. Gold et al., "Stimulation of Protein Tyrosine Phosphorylation by the B–Lymphocyte Antigen Receptor," *Nature* 345:810–813 (1990).
M. C. Cam et al., "In Vivo Antidiabetic Actions of Naglivan, An Organic Vanadyl Compound in Streptozotocin–Induced Diabetes," *Diabetes Res. & Clin. Pract.* 20:111–121 (1993).
A. L. Burkhardt et al., "Anti–Immunoglobulin Stimulation of B Lymphocytes Activates src–Related Protein–Tyrosine Kinases," *Proc. Natl. Acad. Sci. USA* 88:7410–7414 (1991).
F. M. Uckun et al., "Tyrosine Phosphorylation Is a Mandatory Proximal Step in Radiation–Induced Activation of the Protein Kinase C Signaling Pathway in Human B–Lymphocyte Precursors," *Proc. Natl. Acad. Sci. USA* 90:252–256 (1993).
C. P. Stewart & A. L. Prote, "Electron Paramagnetic Resonance Spectra of Some Oxovanadium (IV) Chelates," *J. Chem. Soc. Dalton Trans.* 1661–1666 (1972).
X.-R. Yao & D. W. Scott, "Expression of Protein Tyrosine Kinases in the Ig Complex of Anti–I–Sensitive and Anti–I–Resistant B–Cell Lymphomas: Role of the p55$^{blk}$ Kinase in Signaling Growth Arrest and Apoptosis," *Immunol. Rev.* 132:163–186 (1993).
X.-R. Yao & D. W. Scott, "Antisense Oligodeoxynucleotides to the blk Tyrosine Kinase Prevent Anti–I–Chain–Mediated Growth Inhibition and Apoptosis in a B–Cell Lymphoma," *Proc. Natl. Acad. Sci. USA* 90:7946–7950 (1993).
F. M. Uckun et al., "Ionizing Radiation Stimulates Unidentified Tyrosine–Specific Protein Kinases in Human B–Lymphocyte Precursors, Triggering Apoptosis and Clonogenic Cell Death," *Proc. Natl. Acad. Sci. USA* 89:9005–9009 (1992).
P. J. L. Lane et al., "The Role of Tyrosine Phosphorylation in Signal Transduction Through Surface Ig in Human B Cells," *J. Immunol.* 146:715–722 (1991).

(List continued on next page.)

*Primary Examiner*—Porfirio Nazario-Gonzales
*Attorney, Agent, or Firm*—Merchant, Gould, Smith, Edell, Welter & Schmidt

[57] ABSTRACT

A method of inhibiting the proliferation of B cells by using inhibitors of phosphotyrosine phosphatase can be used to regulate the immune response and to treat diseases such as leukemias or lymphomas marked by malignant proliferation of B cells. The use of such inhibitors can be combined with radiation, which produces a synergistic effect. Several types of inhibitors can be used, including: (1) compounds comprising a metal coordinate-covalently bound to an organic moiety that can form a five- or six-membered ring; (2) compounds in which vanadium (IV) is coordinate-covalently bound to an organic moiety such as a hydroxamate, α-hydroxypyridinone, α-hydroxypyrone, α-amino acid, hydroxycarbonyl, or thiohydroxamate; (3) coordinate-covalent complexes of vanadyl and cysteine or a derivative thereof; (4) nonhydrolyzable phosphotyrosine phosphatase analogues; (5) phostatin; and (6) 4-(fluoromethyl)phenyl phosphate and esterified derivatives. For the metal-containing coordinate covalent compounds, the metal is preferably vanadium (IV).

5 Claims, 12 Drawing Sheets

OTHER PUBLICATIONS

F. M. Uckun et al., "Use of a Novel Colony Assay to Evaluate the Cytotoxicity of an Immunotoxin Containing Pokeweed Antiviral Protein Against Blast Progenitor Cells Freshly Obtained from Patients with Common B–Lineage Acute Lymphoblastic Leukemia," *J. Exp. Med.* 163:347–368 (1986).

M.–A. Campbell & B. M. Sefton, "Protein Tyrosine Phosphorylation is Induced in Murine B Lymphocytes in Response to Stimulation with Anti–Immunoglobulin," *EMBO J.* 9:2125–2131 (1990).

Abstract of a presentation made at the Annual Meeting of the Oxygen Society, Charleston, South Carolina, on Nov. 12–17, 1993, by G. L. Schieven et al., "Identification of Reactive Oxygen Intermediate Responsive Tyrosine Kinases in Lymphocytes.".

Abstract of a presentation made at the Ninth International Symposium on Cellular Endocrinology: "Cell Signalling and the Molecular Stress Response", Lake Placid, New York, Sep. 23–26, 1993, by G. L. Schieven et al., entitled Identification of Reactive Oxygen Intermediate Responsive Tyrosine Kinases in Lymphocytes.

A. Shaver et al., "Insulin–Mimetic Peroxovanadium Complexes: Preparation and Structure of Potassium Oxodiperoxo (pyridine–2–carboxylato) vanadate (V), $K_2[VO(O_2)_2(C_5H_4NCOO)]\cdot 2H_2O$, and Potassium Oxidiperoxo (3–hydroxypyridine–2–carboxylato) vanadate (V), $K_2[VO(O_2)_2(OHC_5H_3NCOO)]\cdot 3H_2O$, and Their Reactions with Cysteine," *Inorg. Chem.* 32: 3109–3113 (1993).

J. P. Secrist et al., "Stimulatory Effects of the Protein Tyrosine Phosphatase Inhibitor, Pervanadate, on T–cell Activation Events," *J. Biol. Chem.* 268:5886–5893 (1993).

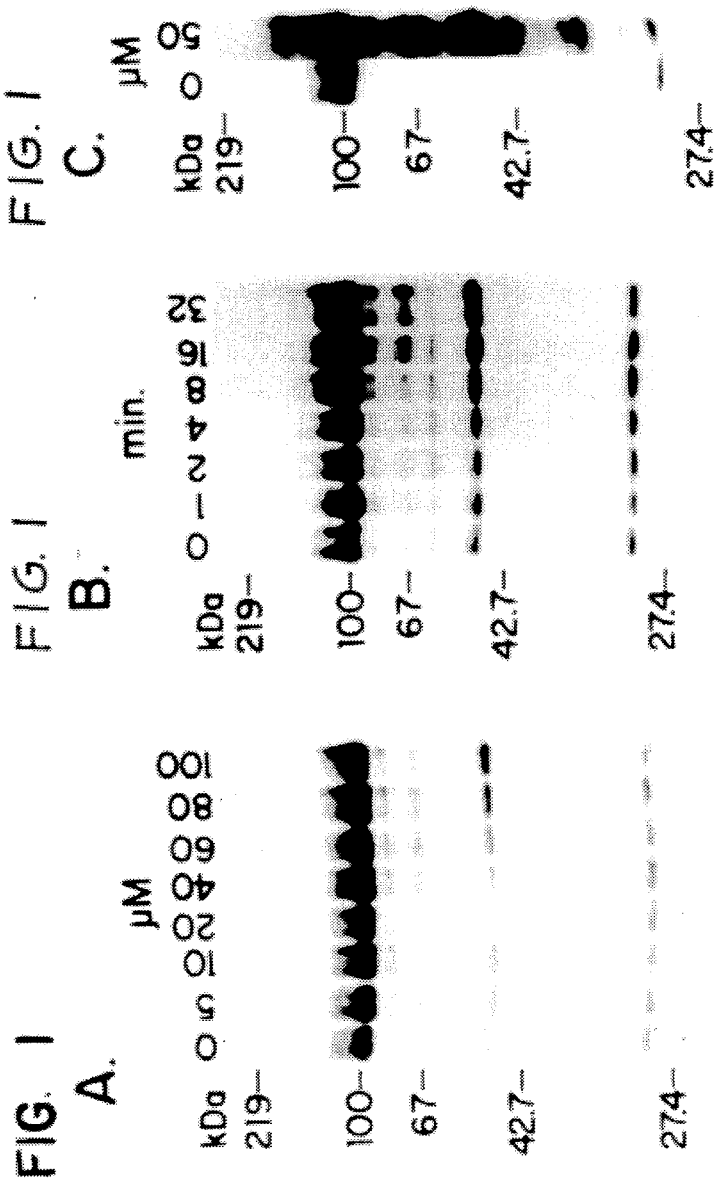

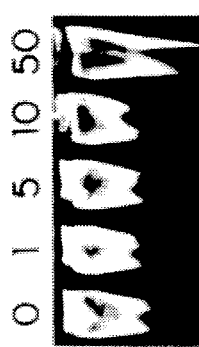
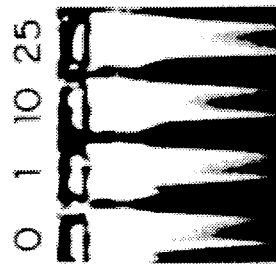
FIG. 2B

USE OF PHOSPHOTYROSINE PHOSPHATASE INHIBITORS FOR CONTROLLING CELLULAR PROLIFERATION

This is a Divisional of application Ser. No. 08/189,330, filed Jan. 31, 1994, now allowed, application(s) are incorporated herein by reference.

BACKGROUND OF THE INVENTION

This invention is directed to the use of phosphotyrosine phosphatase inhibitors for controlling cellular proliferation, particularly proliferation of B lymphocytes.

Tyrosine phosphorylation is known to play an essential role in the control of lymphocyte function. This control is exerted by a network of tyrosine kinases and phosphotyrosine phosphatases.

Two different processes known to induce B cell apoptosis have been shown to act through tyrosine phosphorylation.

Apoptosis is a pattern of programmed cell death that involves the breakup of the cellular DNA and can be recognized by electrophoresis of the DNA of the cells. When apoptosis occurs, the DNA is broken into fragments, which can be detected as a ladder on electrophoresis.

In immature B cells, stimulation of sIgM ( surface immunoglobulin M) by either antigen or anti-immunoglobulin antibodies activates the cells (G. J. V. Nossal, *Annu. Rev. Immunol.* 1:33–62 (1983)) Stimulation of sIg (surface immunoglobulin) on B cells induces tyrosine phosphorylation (M. R. Gold et al., *Nature* 345:810–813 (1990); M. A. Campbell & B. M. Sefton, *EMBO J.* 9:2125–2131 (1990)), which is essential for productive sIg signaling (P. J. L. Lane et al., *J. Immunol.* 146:715–722 (1991)). As a result of sIg stimulation, Src family kinases are activated (A. L. Burkhardt et al., *Proc. Natl. Acad. Sci. USA* 88:7410–7414 (1991)). Furthermore, expression of the Src family tyrosine kinase Blk was found to be essential in B cell lymphomas where sIgM stimulation leads to growth arrest and apoptosis (X. R. Yao and D. W. Scott, *Immunol. Rev.* 132:163–186 (1993)). Thus, on sIgM stimulation, tyrosine kinases such as Blk phosphorylate one or more proteins on tyrosine residues, and once phosphorylated, these proteins are then able to induce apoptosis. However, it has also been shown that the abundant phosphotyrosine phosphatase CD45 is required for sIg signal transduction (L. B. Justement et al., *Science* 252:1839–1842 (1991)).

Ionizing radiation is standard therapy for B cell malignancies such as leukemias and lymphomas. It has been demonstrated that ionizing radiation stimulates B cell tyrosine kinases, triggering apoptosis and clonogenic cell death (F. M. Uckun et al., *Proc. Natl. Acad. Sci. USA* 89:9005–9009 (1992)). In this study, the phosphotyrosine phosphatase inhibitor vanadate, administered alone, was not effective. The activation of tyrosine kinases by ionizing radiation was essential for the induction of apoptosis because the tyrosine kinase inhibitors genistein and herbimycin A blocked the effects of the radiation.

In addition to blocking proliferation of malignant B cells in diseases such as leukemias and lymphomas, in a number of situations it may be desirable to slow the growth and/or differentiation of normal B cells. Such occasions include organ transplantation, in which the immune response, at least in the short term, must be suppressed. Limited control of the proliferation of B cells may also be desirable in the treatment of autoimmune diseases such as rheumatoid arthritis and lupus erythematosus.

Accordingly, there exists a need for improved methods of controlling proliferation of B cells in malignant and nonmalignant conditions without requiring the use of radiation. Such an approach preferably involves the induction of programmed cell death (apoptosis) in susceptible cells.

SUMMARY

I have developed a method of inhibiting the proliferation of B cells by using inhibitors of phosphotyrosine phosphatase.

Several types of inhibitors can be used:

(1) compounds comprising a metal selected from the group consisting of vanadium (IV), copper (II) and gallium (II) coordinate-covalently bound to an organic moiety;

(2) nonhydrolyzable phosphotyrosine analogs selected from the group consisting of N-aryl phosphoramidates, N-aryl phosphorothioates, and N-aryl phosphonates, in which the aryl moiety is optionally substituted at any of the ortho, meta, and para positions, and one or two of the oxygen atoms bound to the phosphorus are optionally esterified;

(3) dephostatin; and (4) optionally esterified 4-(fluoromethyl)phenyl phosphate.

The compounds comprising vanadium (IV), copper (II), or gallium (II) coordinate-covalently bound to an organic moiety can be selected from the group consisting of:

(1) keto-enol tautomers with the keto and enol groups on adjacent carbon atoms that form 5-membered rings including the metal; and (2) beta diketones in which the two keto groups are separated by one carbon atom, that form a 6-membered ring including the metal.

For these types of metal-containing coordinate covalent compounds, the metal is preferably vanadium (IV).

When the organic moiety of the metal-containing coordinate covalent compound is a keto-enol tautomer, the organic moiety is preferably one of maltol, 2-hydroxy-2,4,6-cycloheptatrien-1-one, 3-bromo-2-hydroxy-2,4,6-cycloheptatrien-1-one, 2-hydroxy-4-isopropyl-2,4,6-cycloheptatrien-1-one, 2-hydroxy-4-methyl-2,4,6-cycloheptatrien-1-one, 3 -hydroxy-1,2-dimethyl-4(1H)-pyridone, 3-ethyl-2-hydroxy-2-cyclopenten-1-one, 3,4-dihydroxy-3-cylobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione, 2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, 6-(pyrrolidinomethyl)kojic acid, alpha-acetyl-4-hydroxy-beta-(hydroxymethyl)-3-methoxycinnamic acid gamma-lactone, 4-hydroxy-5-phenyl-4-cyclopenten-1,3-dione, 6-(morpholinomethyl)kojic acid, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 6-(piperidinomethyl)kojic acid, 1,2,7-trihydroxyanthraquinone, 6-(4-methylpiperazinomethyl)kojic acid, fisetin, 3-oxo-4,5,6-trihydroxy-3(H)-xanthene-9-propionic acid, benzoin, 4'-chlorobenzoin, quercetin, morin, myricetin, or 4,4'-dimethylbenzoin.

Most preferably, the organic moiety is maltol, and the compound is bis(maltolato)oxovanadium (IV) ("BMLOV").

When the organic moiety is a beta diketone, the organic moiety is preferably one of acetylacetone, 2-acetyl-1-tetralone, benzoylacetone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thenoyltrifluoroacetone, S-t-butyl-acetothioacetate, 3-acetyl-5-methylhexan-2-one, 3-acetyl-2-heptanone, 2,2-dimethyl-6,6,7,7,8,8-heptafluoro-3,5-octanedione, 4-hydroxy-5-phenyl-4-cyclopenten-1,3-dione, 4,4,4-trifluoro-1-phenyl-1,3-butanedione, 3-acetyl-2-octanone, 1(2-hydroxy-4-methylphenyl)-1,3-butanedione, 1-(2-hydroxy-5-methylphenyl)-1,3-butanedione, 3-benzylidene-2,4-pentanedione, 1-(2-hydroxy-5-methylphenyl)-1,3-pentanedione, 2,2,6,6-tetramethyl-3,5-heptanedione, 3-acetyl-5-hydroxy-2-methylchromone, (+)-3-(trifluoroacetyl)camphor, 4,9-dihydro-6-methyl-5H-furo(3,2-g) (1) benzopyran-4,5,9-trione, 3-(2-nitrobenzylidene)-2,4-pentanedione, 1,3-bis(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione, 2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl) methane, or curcumin.

Most preferably, the organic moiety is acetylacetonate.

Alternatively, the coordinate covalent metal-containing compound can be a compound comprising vanadium (IV) coordinate-covalently bound to an organic moiety of formula I

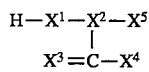

wherein:
(1) $X^1$ and $X^3$ are independently selected from the group consisting of oxygen, sulfur, and $NX^6$;
(2) $X^2$ is selected from the group consisting of nitrogen or $CX^7$; and
(3) $X^4$, $X^5$, $X^6$, and $X^7$ are independently selected from the group consisting of non-labile protons, optionally substituted alkyl groups, optionally substituted aryl groups, optionally substituted aralkyl groups, and optionally substituted alkaryl groups.

Alternatively, the organic moiety can be a compound of formula I wherein at least one pair of $X^4$ to $X^7$ together with the intervening atoms, represents an optionally substituted, saturated or unsaturated homocyclic or heterocyclic ring.

In another alternative, the organic moiety can be a compound of formula I wherein $X^1$ is a $NX^6$ group, $X^4$ is a group $X^8H$ where $X^8$ is selected from the group consisting of oxygen or sulfur, and wherein one proton attached to $X^1$ or $X^8$ is labile.

Suitable compounds of formula I include:
(1) a hydroxamate of formula II;

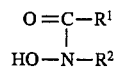

(2) a α-hydroxypyridinone of formula III;

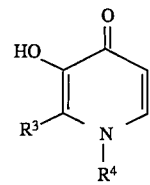

(3) a α-hydroxypyrone of formula IV;

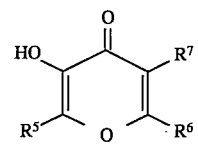

(4) an α-amino acid of formula V;

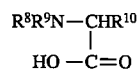

(5) a hydroxycarbonyl of formula VI or formula VII;

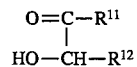

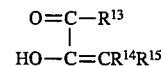

(6) a thiohydroxamate of formula VIII or formula IX, wherein $R^1$ to $R^{19}$ are hydrogen or optionally substituted alkyl.

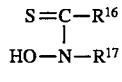

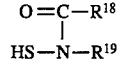

In these formulas, $R^1$ $R^{19}$ are hydrogen or optionally substituted $C_1$–$C_4$ alkyl, e.g., hydroxylated alkyl.

Alternatively, the organic compound can be a coordinate-covalent complex of vanadyl and cysteine or a derivative thereof of formula X

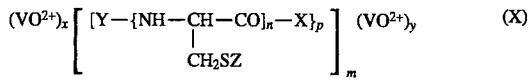

wherein n, p, and m are integers equal to 1 or 2 respectively, and:
(1) when p is equal to 1, then Y is selected from the group consisting of a hydrogen atom and a R'—CO group; and
  (a) when n is equal to 1 and m is equal to 2, X is selected from the group consisting of an OH group, an OR group, and an NHR group wherein R is selected from the group consisting of an alkyl group comprising from 2 to 9 carbon atoms, an aryl group, or an aralkyl group, wherein, when X is an OH group, Y is a R'—CO group wherein R' is selected from the group consisting of an alkyl group comprising from 2 to 9 carbon atoms, and, when X is selected from the group consisting of an OR group and a NHR group, Y is H;
  (b) when n is equal to 2 and m is equal to 1, X is selected from the group consisting of a difunctional amine of formula $WC[CH_2NH-]_2$, a difunctional alcohol of formula $WC[CH_2O-]_2$, and a difunctional amine-alcohol of formula WC(CH$_2$NH—)(CH$_2$O—), wherein W is an alkyl group of from 2 to 9 carbon atoms other than butyl; and (2) when p is equal to 2, then n is equal to 1, m is equal to 1, X is an OH group, and Y is selected from the group consisting of ZCH(CO—)$_2$, —CH$_2$—, or ZCH(CH$_2$—)$_2$ in which Z is an alkyl, aryl, or aralkyl group.

Suitable organic moieties of this type include:

(1) a compound of formula XI;

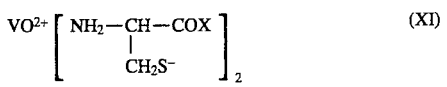

(2) a compound of formula XII;

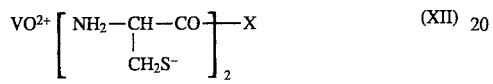

(3) a compound of formula XIII;

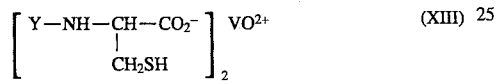

(4) a compound of formula XIV; and

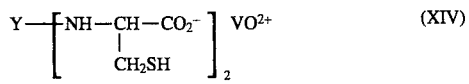

(5) a compound of formula XV.

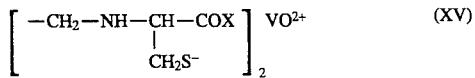

When the phosphotyrosine phosphatase inhibitor is a nonhydrolyzable phosphotyrosine analog, it can be a N-aryl phosphoramidate of formula XVI, in which each of $R_1$ through $R_7$ is selected from the group consisting of hydrogen and $C_1$–$C_5$ alkyl.

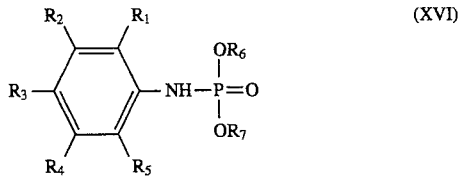

Alternatively, it can be a phosphorothioate of formula XVII in which each of $R_1$ through $R_7$ is selected from the group consisting of hydrogen and $C_1$–$C_5$ alkyl.

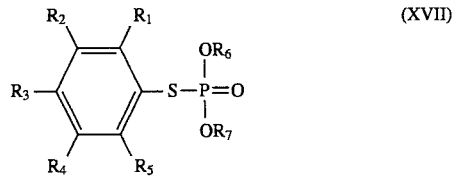

In another alternative, it can be a phosphonate of formula XVIII in which each of $R_1$ through $R_7$ is selected from the group consisting of hydrogen and $C_1$–$C_5$ alkyl.

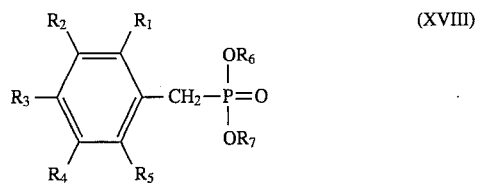

For phosphoramidates of formula XVI, phosphorothioates of formula XVII, or phosphonates of formula XVIII, typically each of $R_1$ through $R_5$ is hydrogen. In that case, at least one of $R_6$ and $R_7$ is preferably other than hydrogen.

Another phosphotyrosine phosphatase inhibitor useful in the methods of the present invention is dephostatin.

Still other phosphotyrosine phosphatase inhibitors are useful in the methods of the present invention, including optionally esterified 4-(fluoromethyl)phenyl phosphates of formula XX, in which $R_1$ and $R_2$ are independently selected from the group consisting of hydrogen and $C_1$–$C_5$ alkyl.

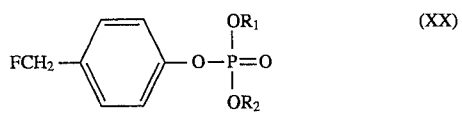

A method for inhibiting B cell proliferation according to the invention comprises the step of contacting proliferating B cells with a phosphotyrosine phosphatase inhibitor as described above, the phosphotyrosine phosphatase inhibitor being administered in a quantity sufficient to detectably inhibit proliferation as measured by incorporation of nucleotides into DNA.

A method of inhibiting phosphotyrosine phosphatase in proliferating B cells according to the invention comprises the step of contacting proliferating B cells with a phosphotyrosine phosphatase inhibitor as described above, the inhibitor being administered to the B cells in a quantity sufficient to inhibit the activity of phosphotyrosine phosphatase in the cells.

Compositions and methods according to the present invention are also useful for studying and/or modifying signaling in T cells, particularly signals involving CD28.

The invention further includes a method of treating a malignant proliferative disorder selected from the group consisting of leukemias and lymphomas wherein the proliferating cells are selected from the group consisting of B cells and myeloid cells. The method comprises the step of contacting the proliferating malignant cells with a phosphotyrosine phosphatase inhibitor as described above, the compound being administered in a quantity sufficient to significantly inhibit proliferation of the malignantly proliferating cells. The method can further include a step of delivering ionizing radiation to the cells contacted with the phosphotyrosine phosphatase inhibitor. The ionizing radiation is delivered in a dose sufficient to induce a substantial degree of cell killing among the malignantly proliferating cells. The degree of cell killing induced is substantially greater than that induced by either the coordinate covalent metal-organic compound or the ionizing radiation alone.

Another aspect of the present invention is a method of preventing the class-switching of antibody-producing cells. The method comprises administering to antibody-producing cells a quantity of a phosphotyrosine phosphatase inhibitor sufficient to detectably reduce the production of IgE antibody by the cells. Typically, the cells also produce IgG antibody, and the quantity of the phosphotyrosine phosphatase inhibitor is such that the ratio of the quantity of IgG antibody produced by the cells to the quantity of IgE antibody produced by the cells increases. A preferred phosphotyrosine phosphatase inhibitor for preventing class-switching is BMLOV.

Yet another aspect of the present invention is novel phosphotyrosine phosphatase inhibitors, including vanadyl 2-acetyl-1-tetralone, vanadyl 2-hydroxy-4-isopropyl-2,4,6-cycloheptatrien-1-one, and vanadyl 2-hydroxy-4-methyl-2,4,6-cycloheptatrien-1-one, cycloheptatrien-1-one.

Additional novel phosphotyrosine phosphatase inhibitors according to the present invention include metal-organic covalent compounds comprising vanadium (IV) coordinate-covalently bound to an organic moiety that is a keto-enol tautomer with the keto and enol groups on adjacent carbon atoms and that forms a 5-membered ring including the metal, the organic moiety being selected from the group consisting of 2-hydroxy-2,4,6-cycloheptatrien-1-one, 3-bromo-2-hydroxy-2,4,6-cycloheptatrien-1-one, 3-hydroxy-1,2-dimethyl-4(1H)-pyridone, 3-ethyl-2-hydroxy-2-cyclopenten-1-one, 3,4-dihydroxyl-3-cyclobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione,2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, alpha-acetyl-4-hydroxy-beta-(hydroxymethyl)-3-methoxycinnamic acid gammalactone, 4-hydroxy-5-phenyl-4-cyclopenten-1,3-dione, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 1,2,7-trihydroxyanthraquinone, fisetin, 3-oxo-4,5,6-trihydroxy-3(H)-xanthene-9-propionic acid, benzoin, 4'-chlorobenzoin, quercetin, morin, myricetin, and 4,4'-dimethylbenzoin.

Additional novel phosphotyrosine phosphatase inhibitors according to the present invention further include metal-organic covalent compounds comprising vanadium (IV) coordinate-covalently bound to an organic moiety that is a beta diketone in which the two keto groups are separated by one carbon atom that forms a 6-membered ring including the metal, the organic moiety being selected from the group consisting of 2-acetyl-1-tetralone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thenoyltrifluoroacetone, S-t-butyl-acetothioacetate, 3-acetyl-5-methylhexan-2-one, 3-acetyl-2-heptanone, 2,2-dimethyl-6,6,7,7,8,8,8-heptafluoro-3,5-octanedione, 4-hydroxy-5-phenyl-4-cyclopenten-1,3-dione, 4,4,4-trifluoro-1-phenyl-1,3butanedione, 3-acetyl-2-octanone, 1 (2-hydroxy-4-methylphenyl)-1,3-butanedione, 1-(2-hydroxy-5-methylphenyl) -1,3-butanedione, 3-benzylidene-2,4-pentanedione, 1-(2-hydroxy-5-methylphenyl)-1,3-pentanedione, 2,2,6,6-tetramethyl -3,5-heptanedione, 3-acetyl-5-hydroxy-2-methylchromone, (+)-3-(trifluoroacetyl)camphor, 4,9-dihydro-6-methyl-5H-furo(3,2 g) (1) benzopyran-4,5,9-trione, 3-(2-nitrobenzylidene)-2,4-pentanedione, 1,3-bis(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione, 2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl) methane, and curcumin.

BRIEF DESCRIPTION OF THE DRAWINGS

These and other features, aspects, and advantages of the present invention will become better understood with reference to the following description, appended claims, and accompanying drawings where:

FIG. 1A is a photograph of an anti-phosphotyrosine western blot following sodium dodecyl sulfate-polyacrylamide electrophoresis of cell lysates from Ramos cells, a human B cell lymphoma cell line, after treatment with bis(maltolato)oxovanadium (IV) (BMLOV), showing the dose dependence of the resulting phosphorylation after a one-hour exposure to BMLOV;

FIG. 1B is a similar photograph of an anti-phosphotyrosine western blot showing the effects of treating the cells with 100 μM BMLOV for varying times;

FIG. 1C is a similar photograph of an anti-phosphotyrosine western blot, showing the high levels of phosphorylation reached after exposure to 50 μM BMLOV for 16 hours;

FIG. 2B is a similar photograph of a stained electropherogram of DNA on an agarose gel of DNA from the human T cell leukemia cell lines Jurkat and CEM, and the human colon carcinoma cell line 3347, after treatment of the cells with BMLOV, showing that apoptosis did not occur, demonstrating the selectivity of BMLOV;

DESCRIPTION

Figure 2A:
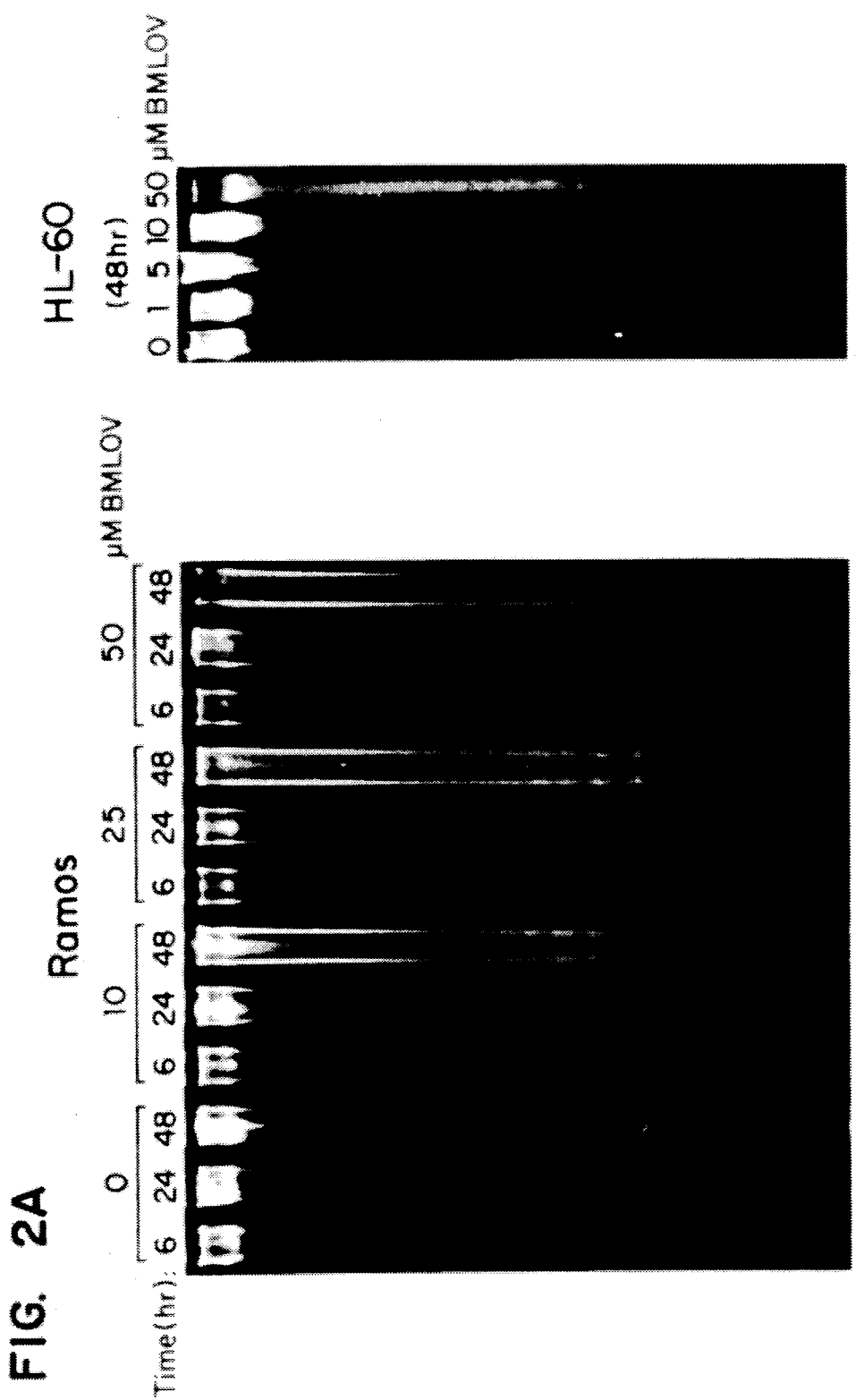
FIG. 2A is a photograph of a stained electropherogramon an agarose gel of DNA from Ramos cells and human promyelocytic leukemia HL-60 cells after treatment of the cells with BMLOV, showing the breakdown of the DNA into fragments characteristic of apoptosis.

I have developed an effective means of inhibiting phosphotyrosine phosphatase, particularly in B cells, as well as novel vanadyl compounds possessing inhibitory activity for phosphotyrosine phosphatase.

The inhibition of phosphotyrosine phosphatase can be used to inhibit the proliferation of both malignant and normal B cells, as well as other physiological functions depending on the balance between phosphorylated and dephosphorylated tyrosine residues.

I. PHOSPHOTYROSINE PHOSPHATASE INHIBITORS

In general, two types of phosphotyrosine phosphatase inhibitors are useful in the methods of the present invention. These are metal-organic coordinate covalent compounds and nonhydrolyzable phosphotyrosine analogs. Other phosphotyrosine phosphatase inhibitors are also useful in the method of the present invention.

A. Metal-Organic Coordinate Covalent Compounds

Metal-organic coordinate covalent compounds useful in the methods of the present invention comprise a metal selected from the group consisting of vanadium (IV), copper (II) and gallium (II) coordinate-covalently bound to an organic moiety that can be either: (1) a keto-enol tautomer with the keto and enol groups on adjacent carbon atoms and that forms a 5-membered ring including the metal; and (2) a beta diketone in which the two keto groups are separated by one carbon atom that forms a 6-membered ring including the metal.

The metal is preferably vanadium (IV). Other metals can give different patterns of inhibition in particular cell types.

If the organic moiety is a keto-enol tautomer forming a 5-membered ring including the metal, it is preferably one of the following moieties: maltol, kojic acid, 2-hydroxy-2,4,6-cycloheptatrien-1-one, 3-bromo-2-hydroxy-2,4,6-cycloheptatrien-1-one, 2-hydroxy-4-isopropyl-2,4,6-cycloheptatrien-1-one, 2-hydroxy-4-methyl-2,4,6-cycloheptatrien-1-one,3-hydroxy-1,2-dimethyl-4(1H)-pyridone, 3-ethyl-2-hydroxy-2-cyclopenten-1-one, 3,4-dihydroxy-3-cyclobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione, 2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, 6-(pyrrolidinomethyl)kojic acid, alpha-acetyl-4-hydroxy-beta-(hydroxymethyl)-3-methoxycinnamic acid gamma-lactone, 4-hydroxy-5-phenyl-4-cyclopenten-1,3-dione, 6-(morpholinomethyl)kojic acid, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 6-(piperidinomethyl)kojic acid, 1,2,7-trihydroxyanthraquinone, 6-(4-methylpiperazinomethyl)kojic acid, fisetin, 3-oxo-4,5,6-trihydroxy-3(H)-xanthene-9-propionic acid, benzoin, 4'-chlorobenzoin, quercetin, morin, myricetin, or 4,4'-dimethylbenzoin. More preferably, the organic moiety is maltol, and the resulting compound is bis(maltolato)oxovanadium (IV) ("BMLOV").

If the organic moiety is a beta diketone, the organic moiety is preferably one of the following moieties: acetylacetone, 2-acetyl-1-tetralone, benzoylacetone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thenoyltrifluoroacetone, S-t-butylacetothioacetate, 3-acetyl-5-methylhexan-2-one, 3-acetyl-2-heptanone, 2,2-dimethyl-6,6,7,7,8,8,8-heptafluoro-3,5-octanedione, 4-hydroxy-5-phenyl-4-cyclopenten-1,3-dione, 4,4,4-trifluoro-1-phenyl-1,3-butanedione, 3-acetyl-2-octanone, 1(2-hydroxy-4-methylphenyl)-1,3-butanedione, 1-(2-hydroxy-5-methylphenyl)-1,3-butanedione, 3-benzylidene-2,4-pentanedione, 1-(2-hydroxy-5-methylphenyl)-1,3-pentanedione, 2,2,6,6-tetramethyl-3,5-heptanedione, 3-acetyl-5-hydroxy-2-methylchromone, (+)-3-(trifluoroacetyl)camphor, 4,9-dihydro-6-methyl-5H-furo(3,2-g)(1) benzopyran-4,5,9-trione, 3-(2-nitrobenzylidene)-2,4-pentanedione, 1,3-bis(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione,2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl) methane, and curcumin. Preferably, the organic moiety is acetylacetone, and the resulting compound is vanadyl acetylacetonate.

Among novel compounds containing vanadium coordinate-covalently bound to an organic moiety that are believed to have activity as phosphotyrosine phosphatase inhibitors are the compounds vanadyl 2-acetyl-1-tetralone, vanadyl 2-hydroxy-4-isopropyl-2,4,6-cycloheptatrien-1-one, and vanadyl 2-hydroxy-4-methyl-2,4,6-cycloheptatrien-1-one.

Other metal-organic coordinate covalent compounds useful for the processes of the present invention include complexes in which the metal is preferably vanadium and the organic moiety is one of formulas I through IX, of which formula I is a general formula and formulas II through IX represent particular classes of compounds of formula I.

$$\begin{array}{c} H-X^1-X^2-X^5 \\ | \\ X^3=C-X^4 \end{array} \quad (I)$$

$$\begin{array}{c} O=C-R^1 \\ | \\ HC-N-R^2 \end{array} \quad (II)$$

(III)

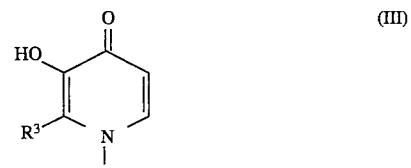

(IV)

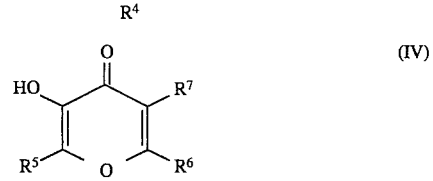

$$\begin{array}{c} R^8R^9N-CHR^{10} \\ | \\ HO-C=O \end{array} \quad (V)$$

$$\begin{array}{c} O=C-R^{11} \\ | \\ HO-CH-R^{12} \end{array} \quad (VI)$$

$$\begin{array}{c} O=C-R^{13} \\ | \\ HO-C=CR^{14}R^{15} \end{array} \quad (VII)$$

$$\begin{array}{c} S=C-R^{16} \\ | \\ HO-N-R^{17} \end{array} \quad (VIII)$$

-continued

In formula I, $X^1$ and $X^3$ are independently oxygen, sulfur, or $NX^6$ preferably oxygen or $NX^6$. $X^2$ is nitrogen or $CX^7$. $X^4$, $X^5$, $X^6$, and $X^7$ are independently non-labile protons or optionally substituted alkyl, aryl, aralkyl or alkaryl. Alternatively, at least one pair of $X^4$ to $X^7$, preferably $X^4$ and $X^5$, together with the intervening atoms can represent an optionally substituted, saturated or unsaturated homocyclic or heterocyclic ring. Alternatively, where $X^1$ is a $NX^6$ group, $X^4$ can represent a group $X^8H$ where $X^8$ is oxygen or sulfur, and one proton attached to $X^1$ or $X^8$ preferably a proton attached to $X^1$, is labile Typical organic moieties of formula I are α-amino acids (other than cysteine), hydroxamates, thiohydroxamates, α-hydroxycarbonyls such as α-hydroxypyridinones or α-hydroxypyrones.

When the organic moiety comprises a homocyclic or heterocyclic ring, the ring is preferably a 5-, 6-, or 7-membered ring. If the ring is heterocyclic, it can contain 1, 2, or 3 heteroatoms, typically 1. The heteroatoms are selected from O, N, and S, and are preferably O or N. Each aryl group is preferably phenyl or naphthyl, typically phenyl. Each alkyl group or moiety contains 1 to 6 carbon atoms, typically 1 to 4. The optional substituents, which do not include thiol groups, are preferably selected from hydroxy, alkoxy, oxo, amide, and amine groups, as well as alkyl groups carrying such substituents. These groups can be selected for their ability to enhance the hydrophilicity or lipophilicity of the complex or to enable the complex to be conjugated to another molecule such as a protein, a polymer, or another biologically active molecule.

Particularly suitable organic moieties include the hydroxamates of formula II, the α-hydroxypyridinones of formula III, the α-hydroxypyrones of formula IV, the α-amino acids of formula V, the hydroxycarbonyls of formulas VI and VII, and the thiohydroxamates of formulas VIII and IX. In these formulas, $R^1$ to $R^{19}$ are hydrogen or optionally substituted, e.g., hydroxylated, $C_1$ to $C_4$ alkyl.

Still other metal-organic coordinate covalent compounds are useful in processes according to the present invention. These coordinate covalent compounds are complexes of vanadyl and cysteine or cysteine derivatives and have the general structure shown in formula X:

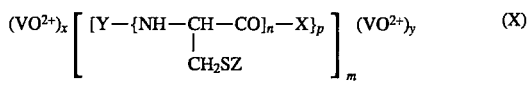

In formula X, either x is 1 and y is 0 or x is 0 and y is 1. The values of n, p, and m are 1 or 2. The cysteine moiety can be D-cysteine or L-cysteine.

When p is equal to 1, then Y is selected from the group consisting of a hydrogen atom and a R'—CO group.

When n is equal to 1 and m is equal to 2, X is selected from the group consisting of an OH group, an OR group, and an NHR group wherein R is selected from the group consisting of an alkyl group comprising from 2 to 9 carbon atoms, an aryl group, or an aralkyl group. In this structure, when X is an OH group, Y is a R'—CO group wherein R' is selected from the group consisting of an alkyl group comprising from 2 to 9 carbon atoms, and, when X is selected from the group consisting of an OR group and a NHR group, Y is H.

When n is equal to 2 and m is equal to 1, X is selected from the group consisting of a difunctional amine of formula $WC[CH_2NH—]_2$, a difunctional alcohol of formula $WC[CH_2O—]_2$, and a difunctional amine-alcohol of formula $WC(CH_2NH—)(CH_2O—)$ wherein W is an alkyl group of from 2 to 9 carbon atoms.

When p is equal to 2, then n is equal to 1, m is equal to 1, X is an OH group, and Y is selected from the group consisting of $ZCH(CO—)_2$, —$CH_2$—, or $ZCH(CH_2—)_2$ in which Z is an alkyl, aryl, or aralkyl group.

One class of compounds of this type has x equal to 1, y equal to 0, and p equal to 1. In this class of compounds, Y is hydrogen and Z is a minus charge. This class of compounds has a free amine group that is bound to the vanadyl; the ligand bound to the vanadyl is bimolecular, in that two organic moieties are complexed to a single vanadyl ion. The ligand has a negative charge on a sulfur atom. This class of compounds is depicted in formula XI.

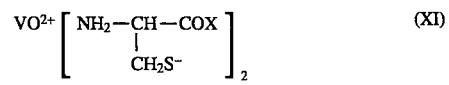

In formula XI, X is an —OR group or a —NHR (amine) group, in which the R moiety is an aryl or aralkyl group or an alkyl group other than methyl. Where X is a —NHR group, the compound is a complex of vanadyl with an amide of cysteine such as a butylamide of cysteine or an octylamide of cysteine. The vanadyl-octylamide complex of L-cysteine is shown in formula XIa.

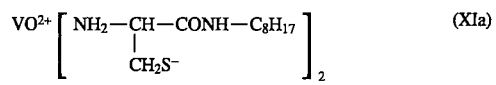

Where X is an —OR group, the compound is, for example, a complex of vanadyl with an ester of the cysteine, such as an octylester of cysteine or a butylester of cysteine.

Another class of compounds of this type has n equal to 2 and m equal to 1. In this class of compounds, the ligand is monomolecular. This class of compounds is depicted in formula XII.

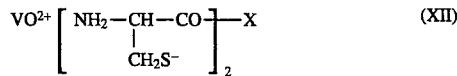

In formula XII, X corresponds to a difunctional amine of formula $WC[CH_2NH—]_2$, a difunctional alcohol of formula $WC[CH_2O—]_2$, or a difunctional amine-alcohol of formula $WC(CH_2NH—)(CH_2O—)$. R is an alkyl group of from 2 to 9 carbon atoms.

Yet another class of compounds of this type has x equal to 0,1 y equal to 1, and n equal to 1. In this class of compounds, X is a $O^-$ group and Z is hydrogen. This class of compounds includes a bimolecular ligand comprising a free carboxyl group and is depicted in formula XIII.

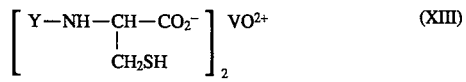

In molecules of formula XIII, Y corresponds to a R—CO (ketone) group in which the R moiety is an alkyl, aryl, or aralkyl group.

Yet another class of compounds of this type has p equal to 2 and m equal to 1. This class of compounds includes a monomolecular ligand comprising two free carboxyl groups and is depicted in formula XIV.

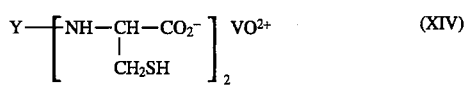

In molecules of formula XIV, Y corresponds to a group of formula $ZCH(CO—)_2$, —$CH_2$—, or $ZCH(CH_2—)$ a in which Z is an alkyl, aryl, or aralkyl group.

Still another class of compounds of this type has x equal to 0, y equal to 1, Y a $CH_2$ group, and Z a minus charge. In this class of compounds, n and p are each 1 and m is 2. This class of compounds includes a monomolecular ligand with substituted amino and carboxyl groups and is depicted in formula XV.

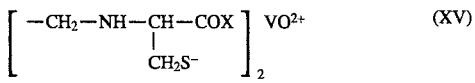

In formula XV, X is an —OR group or a —NHR (amine) group, in which the R moiety is an aryl or aralkyl group or an alkyl group other than methyl.

B. Nonhydrolyzable Phosphotyrosine Analogs

Another class of phosphotyrosine phosphatase inhibitors useful in the methods of the present invention is nonhydrolyzable phosphotyrosine analogs. These analogs can be either: (1) N-aryl phosphoramidates; (2) N-aryl phosphorothioates; or (3) N-aryl phosphonates. The N-aryl phosphoramidates have the structure shown in formula XVI, the N-aryl phosphorothioates have the structure shown in formula XVII, and the N-aryl phosphonates have the structure shown in formula XVIII.

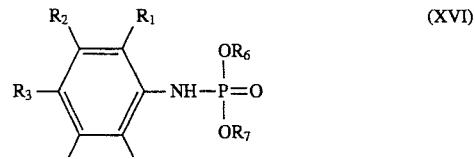

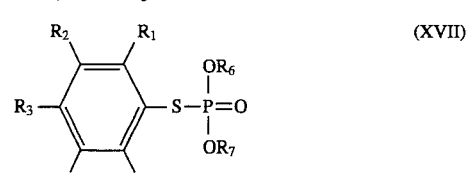

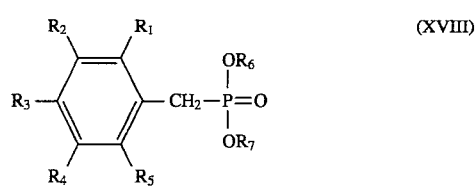

In either the N-aryl phosphoramidates, the N-aryl phosphorothioates, or the N-aryl phosphonates, the aryl moiety can be optionally substituted at any of the ortho, meta, and/or para positions. Similarly, one or two of the oxygen atoms bound to the phosphorus are optionally esterified.

In the N-aryl phosphoramidate of formula XVI, each of $R_1$ through $R_7$ can be selected from the group consisting of hydrogen and $C_1$–$C_5$ alkyl, which can be either straight-chain or branched-chain. Preferably, each of $R_1$ through $R_5$ is hydrogen. Preferably, when each of $R_1$ through $R_5$ is hydrogen at least one of $R_6$ and $R_7$ is other than hydrogen.

When the nonhydrolyzable phosphotyrosine analog is a phosphorothioate of formula XVII, preferably each of $R_1$ through $R_7$ is hydrogen or $C_1$–$C_5$ alkyl, which can be either straight-chain or branched-chain. Preferably, each of $R_1$ through $R_5$ is hydrogen. When each of $R_1$ through $R_5$ is hydrogen, at least one of $R_6$ and $R_7$ is other than hydrogen.

Similarly, when the nonhydrolyzable phosphotyrosine analogue is a phosphonate of formula XVIII, preferably each of $R_1$ through $R_7$ is hydrogen or $C_1$–$C_5$ alkyl, which can be either straight-chain or branched-chain. Preferably, each of $R_1$ through $R_5$ is hydrogen. When each of $R_1$ through $R_5$ is hydrogen, at least one of $R_6$ and $R_7$ is other than hydrogen.

C. Additional Phosphotyrosine Phosphatase Inhibitors

Additional phosphotyrosine phosphatase inhibitors exist that are useful in methods according to the present invention. These additional phosphotyrosine phosphatase inhibitors include dephostatin and 4-(fluoromethyl)phenyl phosphate and its esterified derivatives.

1. Dephostatin

Dephostatin is a phosphotyrosine phosphatase inhibitor isolated from *Streptomyces* sp. MJ742-NF5 (M. Imoto et al., "Dephostatin, a Novel Protein Tyrosine Phosphatase Inhibitor Produced by Streptomyces. I. Taxonomy, Isolation, and Characterization," *J. Antibiotics* 46:1342–1346 (1993)). It has structure XIX shown below

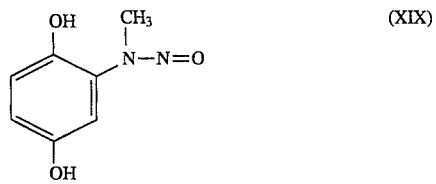

and is a competitive inhibitor of phosphotyrosine phosphatase, competing with the substrate for the enzyme. Dephostatin can be extracted from the broth filtrate of a Streptomyces culture with ethyl acetate and purified by silica gel chromatography and high-pressure liquid chromatography (HPLC).

2. 4-(Fluoromethyl)phenyl Phosphate and Its Esterified Derivatives

The inhibitor of human prostatic acid phosphatase 4-(fluoromethyl)phenyl phosphate (formula XX; $R_1$ and $R_2$ each H) (J. K. Myers & T. S. Widlanski, "Mechanism-Based Inactivation of Prostatic Acid Phosphatase," *Science* 262:1451–1453 (1993)), together with its esterified derivatives, are also phosphotyrosine phosphatase inhibitors that are useful in processes according to the present invention. In compounds of formula XX useful in processes according to the present invention, $R_1$ and $R_2$ are either hydrogen or $C_1$–$C_5$ alkyl, which can be either straight-chain or branched-chain. Preferably, at least one of $R_1$ and $R_2$ is $C_1$–$S_5$ alkyl.

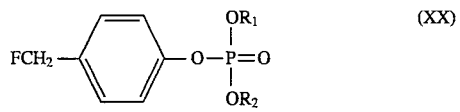

D. Synthesis of Compounds

1. Synthesis Of Metal-Organic Coordinate Covalent Compounds

In general, the metal-organic coordinate covalent compounds are synthesized by the general method described for bis(maltolato)oxovanadium (IV) in J. H. McNeill et al., "Bis(maltolato)oxovanadium (IV) Is a Potent Insulin Mimic," *J, Med. Chem.* 35:1489–1491 (1992). In general, the compounds are prepared by combining the organic ligand (maltol for BMLOV) and vanadyl sulfate in a 2:1 ratio, raising the pH of the solution to 8.5, refluxing overnight, and collecting the compound that precipitates upon cooling.

In the generalization of this method, the organic moiety is dissolved in water at alkaline pH. Depending on the compound, a higher pH may be required for solubilization. For some compounds, a water-miscible, less polar solvent might need to be added to dissolve the compound. Such solvents can include aprotic solvents such as acetonitrile, dimethylsulfoxide, or dimethylformamide, although other suitable solvents are also known in the art. Vanadyl sulfate, or another metal salt if desired, is then added in a sufficient quantity to achieve a 2:1 molar ratio between the organic moiety and the metal salt. The solution is then heated with a condenser attached to the reaction flask to permit refluxing. Following the reaction, the solution is then cooled and the product is recovered as a precipitated solid. In some cases, the product may not precipitate, and can then be recovered by rotary evaporation of the solvent or by other means, such as chromatography.

Vanadium chelates with ligands of Formula I can be prepared in a one-pot synthesis analogous to that described for gallium, aluminum, or indium complexes by Zhang et al., *Can. J. Chem.*, 67:1708–1710 (1989).

In general, the compounds of formula X are synthesized by the following process:

(1) reacting a mono- or bifunctional amine or mono- or bifunctional alcohol, or an amine alcohol, with cysteine or a derivative thereof, which is protected on the amine function and on the thiol function by a t-butyloxycarbonyl group in the presence of dicyclohexylcarbodiimide/hydroxybenzotriazole;

(2) eliminating the butyloxycarbonyl group by acidolysis;

(3) adding a vanadyl sulfate dissolved in water under a nitrogen atmosphere to the hydrochloride of the cysteine derivative in a dimethylformamide-borate buffer mixture at a pH of about 10, with a cysteine:vanadyl ratio of about 5:1;

(4) recovering the precipitated complex; and (5) washing the recovered precipitate with water and drying the precipitate.

A second method for preparing compounds according to formula I having one free amine group or substituted amine and carboxyl groups comprises:

(1) reacting the cysteine or a derivative thereof with vanadyl sulfate at a pH of about 7 in water;

(2) recovering the complex obtained after evaporation;

(3) redissolving the complex in dimethylformamide;

(4) coupling with a mono- or bifunctional amine, a mono- or bifunctional alcohol, or an amine-alcohol, in the presence of dimethylaminopropylethylcarbodiimide; and (5) recovering the complex after vacuum evaporation of the solvent, and washing the complex with ether and with water.

In general, a method for preparing the compounds of formula XI or XV comprises:

(1) reacting a monofunctional amine or a monofunctional alcohol with the cysteine or a derivative thereof protected on the amine function and on the thiol function by a t-butyloxycarbonyl group in the presence of dicyclohexylcarbodiimide/hydroxybenzotriazole;

(2) eliminating the t-butyloxycarbonyl group by acidolysis with the aid of hydrochloric acid and dioxane;

(3) adding vanadyl sulfate which is dissolved in water, under a nitrogen atmosphere, to the solution of the hydrochloride of the cysteine derivative in a dimethylformamide-borate buffer mixture at a pH of about 10 with a cysteine-vanadyl ratio of 5:1;

(4) stirring the mixture for two hours in a nitrogen atmosphere;

(5) recovering the complex formed by precipitation by filtration; and (6) washing with water and drying the precipitate.

Another method for preparing the compounds of formula XI or XV comprises:

(1) reacting the cysteine or derivative thereof with vanadyl sulfate at a pH of about 7 in water;

(2) recovering the complex obtained after evaporation;

(3) redissolving the complex formed in dimethylformamide as above;

(4) coupling with a monofunctional amine or a monofunctional alcohol in the presence of dimethylaminopropylethylcarbodiimide; and (5) recovering the complex after vacuum evaporation of the solvent, washing with ether and with water, dissolving the product in methanol, evaporation, and reprecipitation by ethyl ether.

The preparation of the compound of formula XII comprises reacting a bifunctional amine or a bifunctional alcohol or an amine-alcohol with the cysteine or a derivative thereof. The remaining procedure is identical to that described above for the preparation of compounds XI and XV.

The preparation of the compound of formula XIII where Y corresponds to the RCO— group comprises:

(1) coupling an activated derivative (an ester or an acyl chloride) of the RCOOH acid with a cysteine previously protected on its thiol function by a t-butyloxycarbonyl group;

(2) deprotecting the thiol function by acidolysis; and (3) complexing the resulting N-acylated derivative with the vanadyl sulfate in a DMF-water medium at a pH of 10.

A method for preparing the compound of formula XIV where Y corresponds to $RCH(CO—)_2$, comprises:

(1) coupling an activated derivative (ester or acyl chloride) of the diacid $RCH(COOH)_2$ with a cysteine previously protected on its thiol function with a t-butyloxycarbonyl group;

(2) deprotecting the thiol function by acidolysis;

(3) reducing the N-acylated derivative thus obtained; and (4) complexing the reduced derivative in a DMF-water medium at a pH of 10 in the presence of vanadyl sulfate.

2. Synthesis of Nonhydrolyzable Phosphotyrosine Analogs

The nonhydrolyzable phosphotyrosine analogs, which are phosphoramidates, phosphorothioates, or phosphonates, can be synthesized by methods well understood in the art for synthesis of these compounds. Phosphorothioyltyrosine can be synthesized by sulfurization of the intermediate phosphite triester using phenylacetyl disulfide (D. B. A. Debont et al., "Solid-Phase Synthesis of O-Phosphothioylserine-Containing and O-Phosphorothreonine-Containing Peptides as Well as of O-Phosphoserine-Containing and O-Phosphothreonine-Containing Peptides," *J. Org. Chem.* 58:1309–1317 (1993)). Phosphonates of tyrosine can be synthesized with the use of the reagent 4-[(di-t-butylphosphono)methyl]-N-(fluoren-9-ylmethoxycarbonyl)-D,L-phenylalanine (T. R. Burke et al., "Preparation of Fluoro-4-(Phosphonomethyl)-D,L-Phenylalanine and Hydroxy-4-(Phosphonomethyl)-D,L-Phenylalanine Suitably Protected for Solid-Phase Synthesis of Peptides Containing Hydrolytically Stable Analogues of O-Phosphotyrosine," *J. Org. Chem.* 58:1336–1340 (1993)).

II. USE OF PHOSPHOTYROSINE PHOSPHATASE INHIBITORS

Phosphotyrosine phosphatase inhibitors, including metal-organic coordinate covalent compounds such as vanadyl compounds and nonhydrolyzable phosphotyrosine analogs, can be used to block or alter a number of processes involving phosphotyrosine metabolism.

A. Inhibition of Proliferation of B Cells

In B cells, the level of tyrosine phosphorylation is used for metabolic regulation. Accumulation of an excessive level of tyrosine phosphorylation, such as by the continued activity of tyrosine kinases in the absence of significant phosphotyrosine phosphatase activity, leads to apoptosis, which is programmed cell death marked by fragmentation of cellular DNA. Therefore, the administration of inhibitors of phosphotyrosine phosphatase can be used to control the proliferation of B cells. This is particularly desirable for the treatment of malignancies of B cell origin, such as leukemias and lymphomas. Such treatment also has the effect of sensitizing the cells to ionizing radiation, so that the effect of ionizing radiation and phosphotyrosine phosphatase inhibitors are not additive but synergistic.

However, phosphotyrosine phosphatase inhibitors can also be used to control proliferation of normal B cells, particularly in situations in which down regulation of the immune response is desired. Such situations include induction of immunosuppression to prevent transplant rejection, as well as in the treatment of autoimmune diseases such as rheumatoid arthritis, Hashimoto's thyroiditis, and systemic lupus erythematosus, as well as other autoimmune diseases.

Phosphotyrosine is also involved in proliferation of protozoans, such as amoebae and trypanosomes, a number of species of which are serious parasites. Accordingly, such phosphotyrosine phosphatase inhibitors can also be useful in treating protozoan-based diseases. It is predicted that developmentally stage-specific tyrosine phosphorylation is disrupted in these organisms. This disruption is predicted to lead to death of the protozoa (M. Parsons et al., "Distinct Patterns of Tyrosine Phosphorylation During the Life Cycle of *Trypanosoma brucei*," *Molec. Biochem. Parasitol.* 45:241–248 (1990).

The method of inhibiting B cell proliferation comprises the step of contacting proliferating B cells with a phosphotyrosine phosphatase inhibitor as described above. The compound is administered in a quantity sufficient to detectably inhibit proliferation of the cells as measured by incorporation of nucleotides into DNA. The term "detectably inhibit proliferation," as used herein, refers to a detectable decrease in either DNA synthesis or cell number, inasmuch as cell division follows DNA synthesis. Typically, the dose required is in the range of 1 $\mu$M to 100 $\mu$M, more typically in the range of 5 $\mu$M to 25 $\mu$M. The exact dose required can be readily determined from in vitro cultures of the cells and exposure of the cells to varying doses of the phosphotyrosine phosphatase inhibitor. The effect of the phosphotyrosine phosphatase inhibitor can be judged by clonogenic assays, assays measuring the incorporation of radioactively labelled nucleotides into DNA, or other assays measuring cell proliferation.

B. Treatment of Lymphoproliferative Disorders

Because of the effect of phosphotyrosine phosphatase inhibitors on proliferation of cells, particularly B cells, but also myeloid cells, such inhibitors can be used in a method of treating malignant proliferative disorders. The diseases that can be treated include leukemias and lymphomas, and the proliferating cells can be either B cells, or, alternatively, myeloid cells. The method comprises the step of contacting the proliferating malignant cells with a phosphotyrosine phosphatase inhibitor as described above. The compound is administered in a quantity sufficient to significantly inhibit proliferation of the malignantly proliferating cells, as that term is defined above. The dosage range in general will be as described above. Further guidance for the dosage is given in the Examples below.

The compositions can be administered using conventional modes of administration including, but not limited to, intravenous, intraperitoneal, oral, or intralymphatic. Oral or intraperitoneal administration is generally preferred.

The compositions can be in a variety of dosage forms which include, but are not limited to, liquid solutions or suspensions, tablets, pills, powders, suppositories, polymeric microcapsules or microvesicles, liposomes, and injectable or infusible solutions. The preferred form depends on the mode of administration and the quantity administered.

The compositions for administration including the phosphotyrosine phosphatase inhibitors preferably also include conventional pharmaceutically acceptable carriers and adjuvants known in the art such as human serum albumin, ion exchanges, alumina, lecithin, buffer substances such as phosphates, glycine, sorbic acid, potassium sorbate, and salts or electrolytes such as protamine sulfate.

The most effective mode of administration and dosage regimen for the phosphotyrosine phosphatase inhibitors as used in the methods of the present invention depend on the severity and course of the disease, the patient's health, the response to treatment, the particular type of malignantly proliferating cells characteristic of the particular leukemia or lymphoma, pharmacokinetic considerations such as the condition of the patient's liver and/or kidneys that can affect the metabolism and/or excretion of the administered phosphotyrosine phosphatase inhibitors, and the judgment of the treating physician. Accordingly, the dosages should be titrated to the individual patient. Nevertheless, an effective dose of the phosphotyrosine phosphatase inhibitors for use in the treatment methods of the present invention can be in the range of from about 1 $\mu$M to about 100 $\mu$M in the blood and/or tissues.

Preferably, the dose of phosphotyrosine phosphatase inhibitor used is sufficient to induce apoptosis in the malignantly proliferating cells.

The treatment method can further comprise a step of delivering ionizing radiation to the cells contacted with the phosphotyrosine phosphatase inhibitor. The ionizing radiation is delivered in a dose sufficient to induce a substantial degree of cell killing among the malignantly proliferating cells, as judged by assays measuring viable malignant cells. The degree of cell killing induced is substantially greater than that induced by either the phosphotyrosine phosphatase inhibitor alone or the ionizing radiation alone. Typical forms of ionizing radiation include beta rays, gamma rays, alpha particles, and X-rays. These can be delivered from an outside source, such as an X-ray machine or a gamma camera, or delivered to the malignant tissue from radionuclides administered to the patient. The use of radionuclides is well understood in the art and need not be detailed further. A range of dosages that can be used is between about 1 and 500 cGy (i.e., from about 1 to about 500 rads).

C. Inhibition of Phosphotyrosine Phosphatases

Methods according to the present invention can also be used to inhibit phosphotyrosine phosphatases for purposes other that that of treating malignant disease. In particular, phosphotyrosine phosphatase inhibitors can be used to suppress the immune system in order to prevent organ or tissue rejection during transplantation and also in the treatment of autoimmune diseases such as rheumatoid arthritis, Hashimoto's thyroidiris, systemic lupus erythematosus, Guillain-Barre Syndrome, and possibly multiple sclerosis.

Methods according to the present invention can also be used in the treatment of protozoan infections, such as amoebae and trypanosomes, whose proliferation also depends on phosphorylation.

Additionally, methods according to the present invention can be useful in the study of B cells in culture, in order to determine their susceptibility to ionizing radiation and other reagents, such as alkylating agents and intercalating agents, that can interfere with DNA synthesis. In particular, methods according to the present invention can be used to block B cell development in vitro in order to determine the effect of inhibition of proliferation of B cells on development of immune responses. For example, such methods could be used to augment signals and enhance calcium levels in cells (see Example 8). Such methods can also be used to block the effects of CD28. Accordingly, such methods can therefore be used to screen B cell cultures for abnormal UV-induced signals. Such screening could be clinically useful in determining susceptibility to conditions related to ultraviolet exposure, such as skin cancer.

D. Prevention of Class-Switching in Antibodies

Methods according to the present invention can further be used to prevent class-switching in antibodies from IgG or IgM to IgE. It is desirable to block IgE production because this type of antibody mediates many allergic responses, particularly immediate-type hypersensitivity reactions such as anaphylaxis, atopy, and urticaria. The CD40 ligand gp39 and the cytokine IL-4 act on B cells to induce the switching of the type of antibody produced from IgM to IgE. CD40 and IL-4 mechanisms of action are known to involve tyrosine phosphorylation. Phosphotyrosine phosphatase inhibitors such as BMLOV disrupt the normal pattern of tyrosine phosphorylation, disrupting the class-switching process. The administration of BMLOV, in particular, can markedly inhibit the production of IgE antibody while much less markedly inhibiting the production of IgG subclasses such as IgG1 and IgG4. This leads to the result that the ratio of IgG to IgE increases (Example 14). This result leads to the conclusion that phosphotyrosine phosphatase inhibitors such as BMLOV have value in the treatment of allergy.

Accordingly, a method of preventing the class-switching of antibody-producing cells comprises administering to antibody-producing cells a quantity of a phosphotyrosine phosphatase inhibitor sufficient to detectably reduce the production of IgE antibody by the cells. Typically, the cells also produce IgG antibody, and the quantity of the phosphotyrosine phosphatase inhibitor is such that the ratio of the quantity of IgG antibody produced by the cells to the quantity of IgE antibody produced by the cells increases.

Any of the phosphotyrosine phosphatase inhibitors disclosed above can be used to prevent class-switching, including metal-organic coordinate covalent compounds, nonhydrolyzable phosphotyrosine analogs, dephostatin, and 4-(fluoromethyl)phenyl phosphate and its esterified derivatives. However, a preferred phosphotyrosine phosphatase inhibitor for preventing class-switching is BMLOV.

The invention is illustrated by the following Examples. The Examples are for illustrative purposes only and are not intended to limit the invention.

EXAMPLES

Example 1

Inhibition of Phosphotyrosine Phosphatases by Bis(Maltolato)Oxovanadium (IV) (BMLOV)

Bis(maltolato)oxovanadium (IV) (BMLOV) was synthesized as described in J. H. McNeill et al., "Bis(maltolato)oxovanadium (IV) is a Potent Insulin Mimic," *J. Med. Chem.* 35:1489–1491 (1992). Briefly, the compound was synthesized by combining maltol (3-hydroxy-2-methyl-4-pyrone) and vanadyl sulfate in a 2:1 ratio in water. The pH of the solution was raised to 8.5, and the solution was refluxed overnight. A deep purple-green birefringent compound precipitated on cooling and was collected. This compound is the BMLOV.

BMLOV was then assayed for its activity in inhibiting several phosphatases, including phosphotyrosine phosphatases PTP1B and CD45, as well as serine/threonine phosphatases PP1 and PP2A and calf intestinal alkaline phosphatase.

The tyrosine phosphatases PTP1B and CD45 were assayed with phosphorylated myelin basic protein as described in K. Guan et al., *Nature* 350:359–362 (1991) except that 2-minute assays were performed. The PTP1B used was a GST fusion protein (Upstate Biotechnology, Lake Placid, N.Y.). The CD45 was immunoprecipitated from Jurkat T cells with the monoclonal antibody 9.4 (ATCC No. HB 10270, deposited with the American Type Culture Collection, Rockville, Md., on Oct. 20, 1989). The phosphatases PP1 and PP2A (Upstate Biotechnology) and calf intestinal alkaline phosphatase (Sigma, St. Louis, Mo.) were assayed with p-nitrophenyl phosphate as a substrate.

The results are shown in Table 1.

TABLE 1

Phosphatase Inhibition by BMLOV

| Phosphatase | $IC_{50}$, NM | SEM | n |
|---|---|---|---|
| PTPIB | 26 | 7 | 3 |
| CD45 | 25 | 1 | 3 |
| PPI | 6156 | 360 | 2 |
| PP2A | 3337 | 208 | 2 |
| Alkaline Phosphatase | $>5 \times 10^5$ | — | 2 |

BMLOV was found to be a potent inhibitor of PTP1B and CD45, both of which are phosphotyrosine phosphatases. The drug showed substantial selectivity for the phosphotyrosine phosphatases relative to other phosphatases. Much higher concentrations of the drug were required to inhibit the serine phosphatases PP1 and PP2A. Intestinal alkaline phosphatase was highly resistant to inhibition by BMLOV.

Example 2

Induction of Tyrosine Phosphorylation in Transformed Lymphocytes

Ramos cells, a human B cell lymphoma cell line, were treated with varying doses of BMLOV. The cells were lysed and lysates were subjected to polyacrylamide gel electrophoresis in the presence of sodium dodecyl sulfate (SDS-PAGE). The resulting electropherograms were subjected to Western blotting with anti-phosphotyrosine antibody to detect the presence of phosphotyrosine in the cells.

The results are shown in FIGS. 1A–1C. FIG. 1A demonstrates that BMLOV induces tyrosine phosphorylation in a dose-dependent manner when the cells were treated with varying doses for a period of 1 hour. FIG. 1B shows the effects of treating cells with 100 μM BMLOV for varying times. The drug was found to begin to induce tyrosine phosphorylation in the cells by 8 minutes and the phosphorylation increased with further exposure.

FIG. 1C demonstrates that treatment of the cells for 16 hours with 50 μM BMLOV leads to high levels of tyrosine phosphorylation.

Example 3

Induction of Apoptosis by BMLOV

BMLOV was demonstrated to kill malignant leukemia and lymphoma cells by inducing apoptosis. Apoptosis is the process of programmed cell death. The hallmark of apoptosis is the fragmentation of DNA into fragments whose size distribution is observed as a ladder of bands on agarose gels. FIG. 2A demonstrates that BMLOV induced apoptosis in Ramos B cell lymphoma cells by 48 hours at a dose of 10 μM, with apoptosis apparent at 24 hours with higher doses. Apoptosis was also observed to be induced in the human acute promyelocytic leukemia cell line HL60 in a dose dependent manner (FIG. 2A). The induction of apoptosis was specific in that apoptosis was not observed in the human T-cell leukemia cell lines CEM or Jurkat, nor was it observed in the human colon carcinoma cell line 3347 (FIG. 2B).

For these experiments, cell samples ($2 \times 10^6$ cells) were centrifuged at 200× g, the media removed by aspiration and the cell pellets stored at −70° C. until processing. Cell pellets were resuspended in 300 μl digestion buffer (100 mM NaCl, 10 mM Tris-HCl, pH 8.0, 25 mM EDTA, 0.5% SDS, 0.1 mg/ml protease K) and incubated for 12 hours at 50° C. DNase-free ribonuclease (5 μg) in 200 μl TE buffer (10 mM Tris-HCl, pH 7.5, 1 mM EDTA) was added to each sample followed by incubation for 2 hours at 37° C. DNA was then extracted once with phenol:chloroform, once with chloroform and then precipitated with 0.5 volumes of ammonium acetate and 2 volumes of ethanol at −70° C. for 12 hours. The precipitated DNA was resuspended in 200 μl TE buffer and quantitated by absorbance at 260 nanometers. The DNA (15 μg) was applied to a 1.3% agarose gel in TBE buffer (89 mM Tris base, 89 mM boric acid, 2 mM EDTA) resolved at 20 mA constant current and the DNA was visualized by staining with ethidium bromide. Fragmented DNA due to apoptosis appeared as a ladder of bands on the gel.

Example 4

Selective Cytotoxicity of BMLOV as Examined in Clonogenic Assays

The selective cytotoxicity of BMLOV was examined in clonogenic assays. Cells were grown in methylcellulose media and the number of colonies formed after seven days of treatment with various doses of the drug were determined. The clonogenic assays were performed with six replicates for each treatment as described [F. M. Uckun et al., *J. Exp. Med.* 163:347–368 (1986); F. M. Uckun & J. A. Ledbetter, *Proc. Natl. Acad. Sci. USA* 85:8603–8607 (1988)). The data is given plus/minus the standard error of the mean.

The data is shown in Table 2. The three B-cell lines, Ramos, RaJi, and REH, were all highly sensitive to doses of 5 to 10 μM BMLOV. The myeloid cell line THP-1 and the promyelocytic cell line HL-60 also were highly sensitive to BMLOV at a dose of only 1 μM. BMLOV gave 99.8% clonogenic cell death for the RaJi transformed B cell line at a dose of 10 μM, and 99.4% clonogenic cell death for HL-60 promyelocytic leukemia cells at 1 μM.

TABLE 2

Inhibition of Leukemia and Lymphoma Cell Line Growth by BMLOV as Measured in Clonogenic Assays

| Dose, μM | Cell Line | | | | |
|---|---|---|---|---|---|
| | Ramos | Raji | REH | THP-1 | HL-60 |
| 0 | 4065 ± 840 | 3252 ± 672 | 5122 ± 1296 | 6453 ± 1563 | 5122 ± 1241 |
| 1.0 | 179 ± 33 (95.6%) | 1291 ± 283 (60.3%) | 1810 ± 385 (64.7%) | 1613 ± 235 (75.0%) | 31 ± 8 (99.4%) |
| 5.0 | 7 ± 2 (99.8%) | 4 ± 0.6 (99.9%) | 71 ± 8 (98.6%) | 127 ± 35 (98.0%) | 31 ± 8 (99.4%) |
| 10.0 | 0 | 3 ± 0.8 (99.9%) | 8 ± 1 (99.8%) | 127 ± 35 (98.0%) | 15 ± 4 (99.7%) |

Data is given in colonies per $10^4$ cells; the percentage of inhibition is shown in parentheses.

By contrast, the T cell line CEM or MDAMB-453 breast carcinoma cells were inhibited only moderately by a dose as high as 100 μM of BMLOV.

Example 5

The Effect of BMLOV on Incorporation of Nucleotides into DNA

In order to determine the effects of BMLOV on various cell types, including a number of cell types that did not grow well in the methylcellulose clonogenic assay, the cells were grown for seven days in the presence of BMLOV. For each cell type, the cells were passaged uniformly for all drug doses given during the seven-day period. The cells were then pulsed for six hours with [$^3$H]thymidine. The extent of DNA synthesis was then determined by counting the radioactivity incorporated into the cells. The data is shown in Table 3.

TABLE 3

Inhibition of Leukemia and Lymphoma Cell Line Growth by BMLOV as Measured in Thymidine Incorporation Assays

| Dose, μM | [$^3$H] cpm Incorporation for Cell Line: | | | | | | |
|---|---|---|---|---|---|---|---|
| | Ramos | BCL$_1$ | A20 | THP-1 | HL-60 | Jurkat | CEM |
| 0 | 292342 | 271144 | 389480 | 202301 | 249183 | 143917 | 395157 |
| 1 | 289936 | 265036 | 419947 | 201670 | 191637 | 149950 | 368721 |
| 5 | 65545 | 226714 | 289932 | 178290 | 276505 | 118720 | 403576 |
| 10 | 167 | 55396 | 66157 | 199993 | 222178 | 98057 | 371256 |
| 25 | 149 | 195 | 281 | 112209 | 11398 | 26511 | 313714 |

Ramos cells were highly sensitive to doses of 10 and 25 μm BMLOV. The murine cell line BCL$_1$ is a highly tumorigenic and lethal leukemia considered to be a model of human chronic lymphocytic leukemia (CLL). These cells were highly sensitive to the drug at a dose of 25 μM. THP-1 cells showed only partial sensitivity to the drug at a dose of 25 μM. In general, cells were more sensitive to the drug in the clonogenic assays than in the thymidine incorporation assay. These results suggest a greater requirement for phosphatase activity for cells to grow as colonies in methylcellulose relative to growth in free suspension in liquid media. The murine B cell lymphoma line A20, which forms highly aggressive tumors in mice, was very sensitive to a dose of 25 μM of the drug. The human promyelocytic leukemia cell line HL60 and the human acute T cell leukemia cell line Jurkat were moderately sensitive to BMLOV at a dose of 25 μM, whereas the human T cell acute lymphocytic leukemia CEM was resistant. These results indicate that malignant cells of B cell origin, including lymphoma, acute lymphocytic leukemia, and chronic lymphocytic leukemia are sensitive to BMLOV. Some leukemias of myeloid and T cell origin also show sensitivity to BMLOV whereas others are resistant.

Example 6

Effect of BMLOV on Normal B Cell Proliferation

Figure 3:
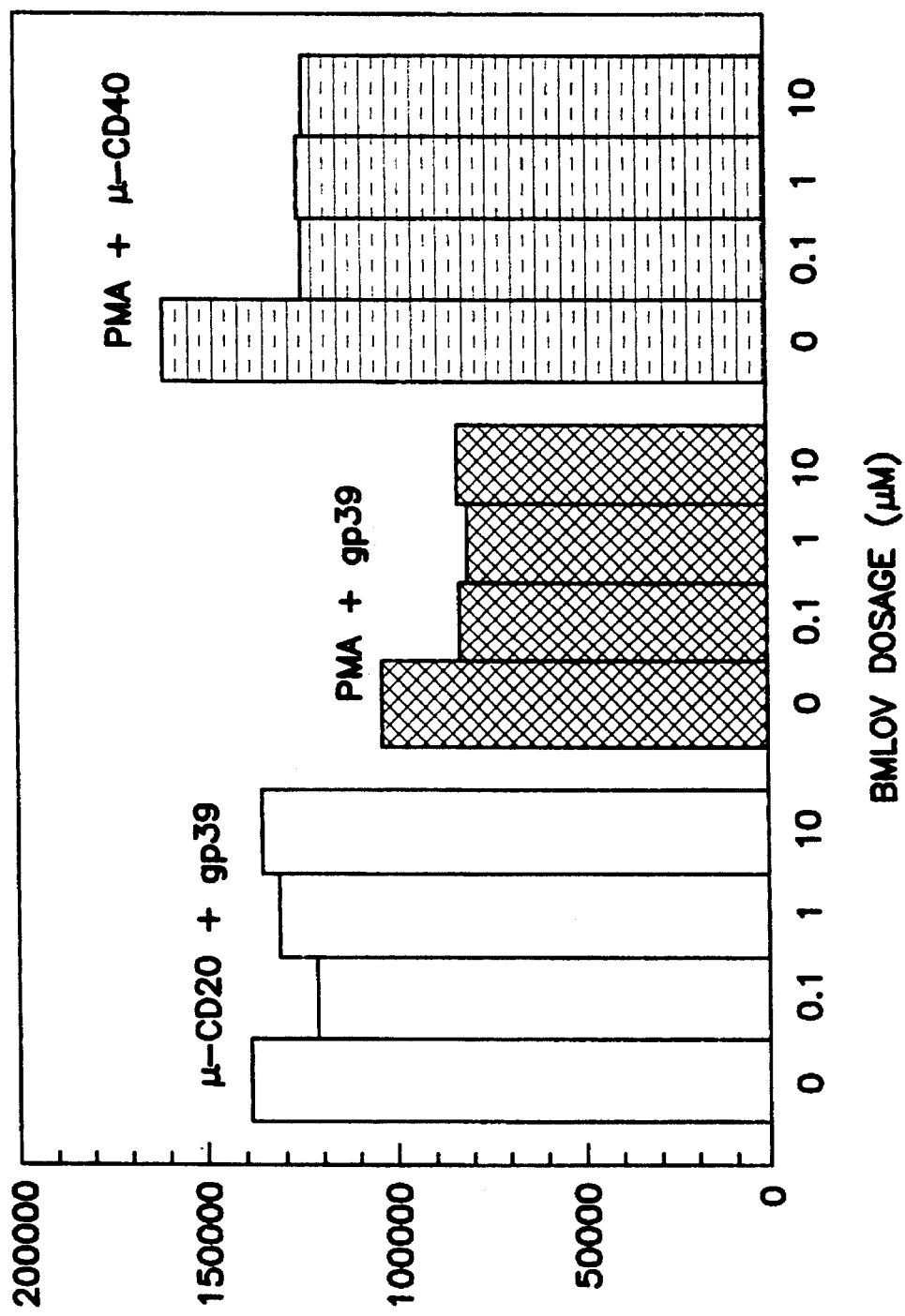
FIG. 3 is a graph showing the effects of varying doses of BMLOV on thymidine incorporation in normal tonsillar cells stimulated with varying combinations of ligands.
Figure 4:
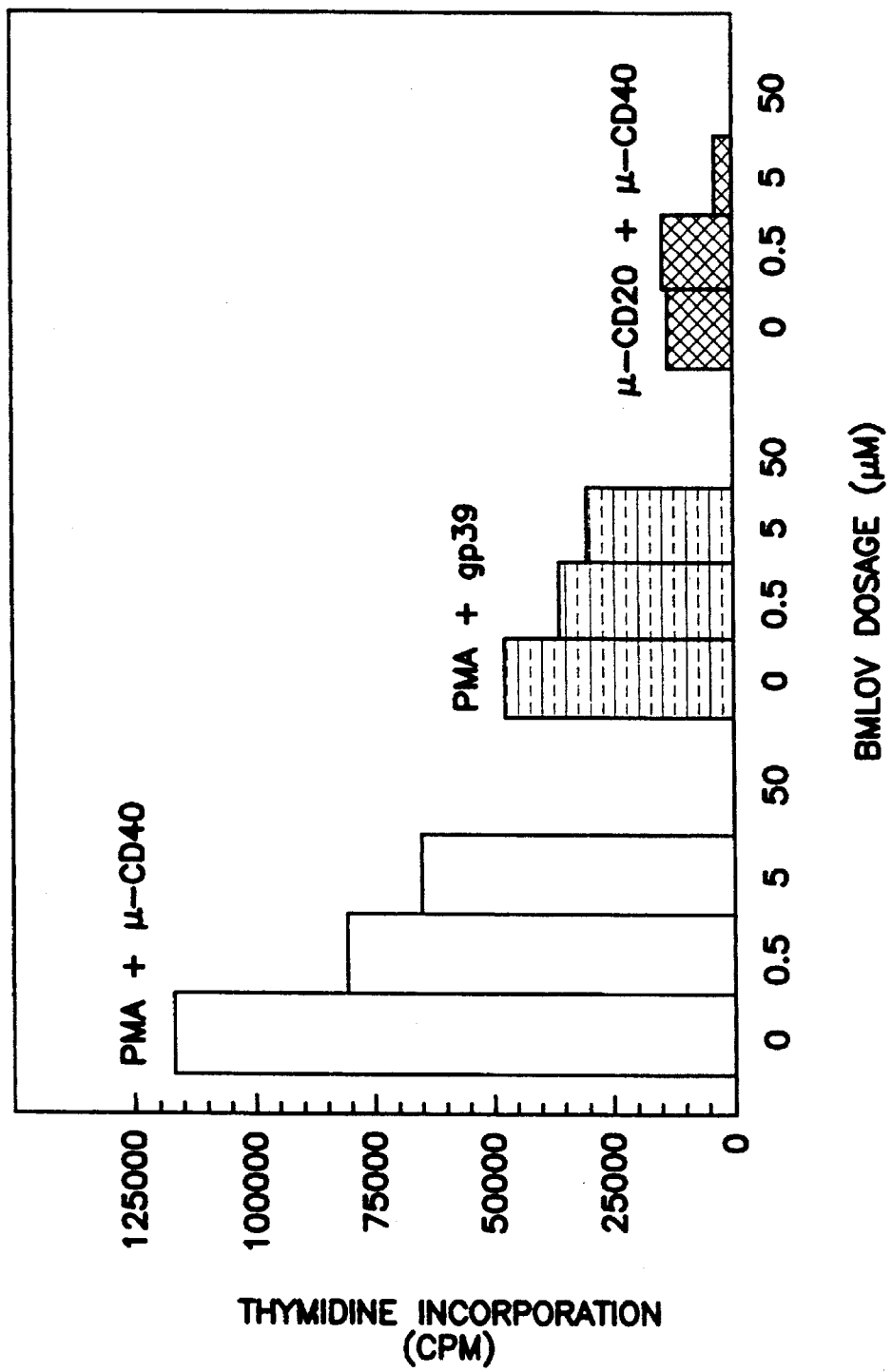
FIG. 4 is a similar graph showing the effects of varying doses of BMLOV on thymidine incorporation with tonsillar cells from a second donor.

BMLOV can inhibit normal tonsillar B cell proliferation driven by stimulation of CD40 via either anti-CD40 antibody or gp39 ligand plus either anti-CD20 antibody or phorbol 12-myristate 13-acetate (PMA). In one experiment, doses of 0.1 to 10 μM had little effect on proliferation (FIG. 3). In a second experiment, a dose of 5 μM gave substantial inhibition of proliferation and a dose of 50 μM completely blocked proliferation (FIG. 4). Variations between the individuals from which the tonsils were derived could account for the differences between these experiments.

Similarly, BMLOV can inhibit the proliferation of normal peripheral B cells. Normal B cell proliferation is mediated in part by the B cell surface molecule CD20, the B cell surface molecule CD40 in conjunction with its ligand gp39, and by the cytokine IL-4. The pharmacologic agent phorbol 12-myristate 13-acetate (PMA) can also be used in combination with these biological stimulation agents to further increase proliferation.

In the experiment reported in Table 4, monoclonal antibodies to CD20 and CD40 were used to stimulate proliferation. Peripheral B cells were isolated from two healthy human volunteers. The cells were stimulated as listed in Table 4 and the effects of various doses of BMLOV on proliferation, as measured by [$^3$H]thymidine incorporation, were determined. BMLOV was able to inhibit proliferation induced by CD20, CD40, IL-4 and PMA in the various combinations tested. The cells from donor 2 were more sensitive, indicating some variation among individuals in their sensitivity to the drug.

It is important to note that the extent to which the proliferation of normal B cells was inhibited in this example (Table 4) was less than for the B cell leukemia and lymphoma cells examined in Examples 4 and 5. Phosphotyrosine phosphatase inhibitors such as BMLOV thus have the potential to act more selectively on malignant B cells than on normal B cells, offering an important advantage in the treatment of leukemia and lymphoma.

TABLE 4

INHIBITION OF NORMAL PERIPHERAL B CELL GROWTH BY BMLOV As MEASURED IN [$^3$H]-THYMIDINE INCORPORATION ASSAYS

| Dose, μm | [$^3$H]cpm Incorporation For Stimuli: | | | |
|---|---|---|---|---|
| | PMA + CD40 | CD20 + CD40 | PMA + IL4 | CD40 + IL4 |
| Donor #1: | | | | |
| 0 | 65587 | 3574 | 61941 | 32499 |
| 1 | 62643 | 3619 | 61415 | 31966 |
| 5 | 58418 | 3644 | 48724 | 33845 |
| 10 | 45330 | 3422 | 45278 | 31637 |
| 25 | 25536 | 2432 | 14277 | 24933 |

TABLE 4-continued

INHIBITION OF NORMAL PERIPHERAL B CELL GROWTH BY BMLOV
As MEASURED IN [³H]-THYMIDINE INCORPORATION ASSAYS

| Dose, μm | [³H]cpm Incorporation For Stimuli: | | | |
|---|---|---|---|---|
| | PMA + CD40 | CD20 + CD40 | PMA + IL4 | CD40 + IL4 |
| Donor #2: | | | | |
| 0 | 52672 | 5602 | 62228 | 19095 |
| 1 | 49102 | 4593 | 53642 | 16597 |
| 5 | 47624 | 5681 | 41892 | 18824 |
| 10 | 29024 | 5269 | 20313 | 12662 |
| 25 | 15671 | 856 | 2730 | 6013 |

Standard error did not exceed 8% for donor 1 and 15% for donor 2. Stimulation of CD20 was via monoclonal antibody 1F5 and stimulation of CD40 was via monoclonal antibody G28-5.

Example 7

Sensitization of Ramos B Cells to Ionizing Radiation by BMLOV

Ionizing radiation in conjunction with bone marrow transplantation is a major therapy for leukemia. However, many leukemias are resistant to radiation, limiting the efficacy of this therapy.

It was previously demonstrated that ionizing radiation stimulates tyrosine kinases in human B lymphocyte precursors, triggering apoptosis and clonogenic cell death, an effect that was markedly enhanced by the phosphatase inhibitor orthovanadate.

Figure 5:
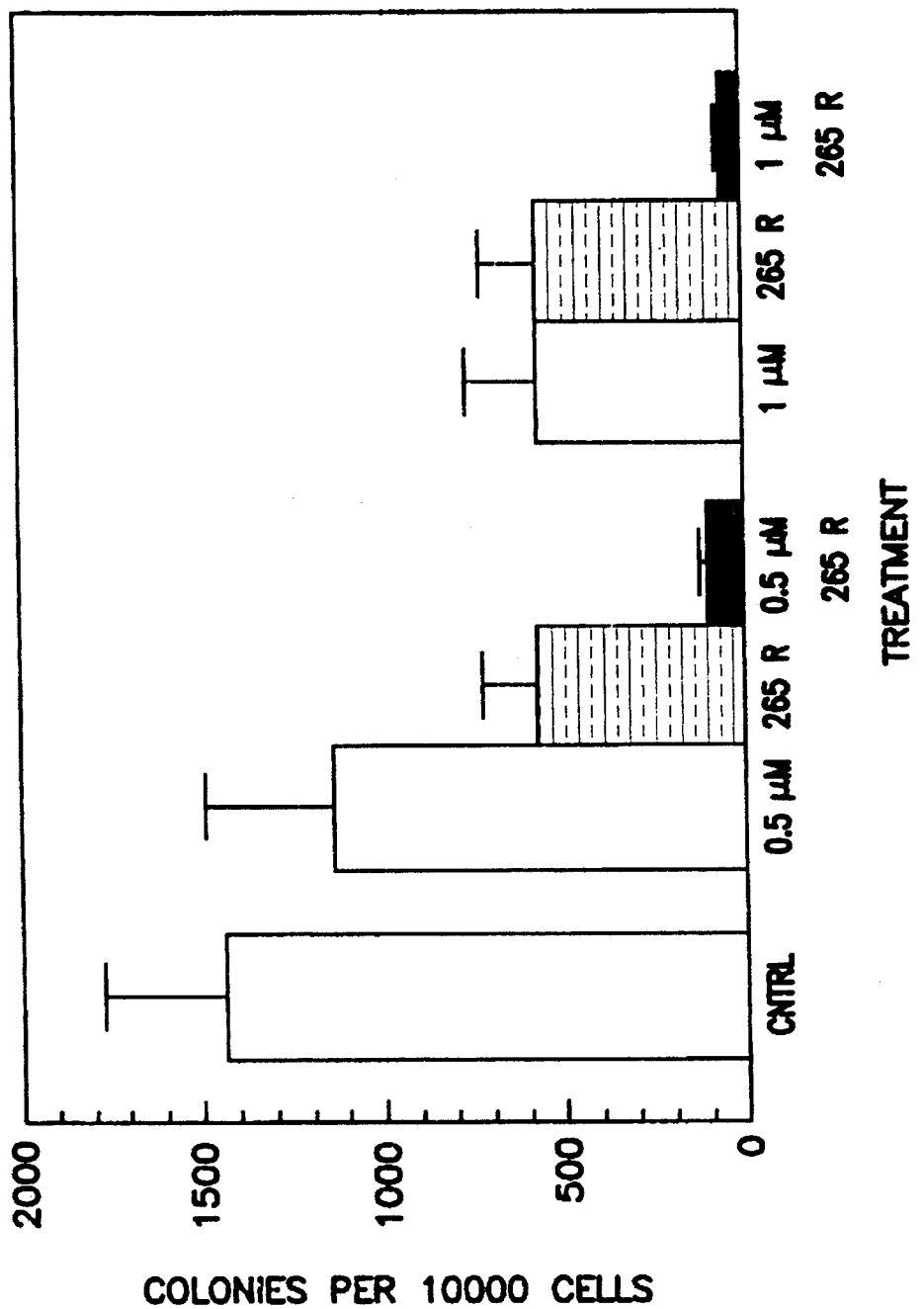
FIG. 5 is a graph showing the results of clonogenic assays after treatment of Ramos B cells with radiation alone, BMLOV alone, or radiation and BMLOV.

In clonogenic assays, as shown in FIG. 5, the combination of 1 μM BMLOV with 265 cGy radiation gave a 10-fold increase in cell death relative to radiation alone. The combination of 2 μM BMLOV with 265 cGy radiation gave a 50-fold increase in clonogenic cell death relative to radiation alone. These effects were synergistic rather than additive in that an approximately 5-fold enhancement in sensitization for the combination treatment was observed relative to expected additive effects based on the use of either treatment alone. These results suggest that phosphatase inhibitors such as BMLOV can be of value for use in combination with radiation therapy for the treatment of B cell malignancies.

Example 8

Inhibition by BMLOV of CD28-Mediated $Ca^{2+}$ Signals and Cell Proliferation

BMLOV reproducibly caused marked inhibition of CD28 $Ca^{2+}$ signals in PHA T cell blasts. The inhibition was specific in that such inhibition was not observed for signals generated by CD3 alone or in combination with CD2 or CD4.

Figure 6:
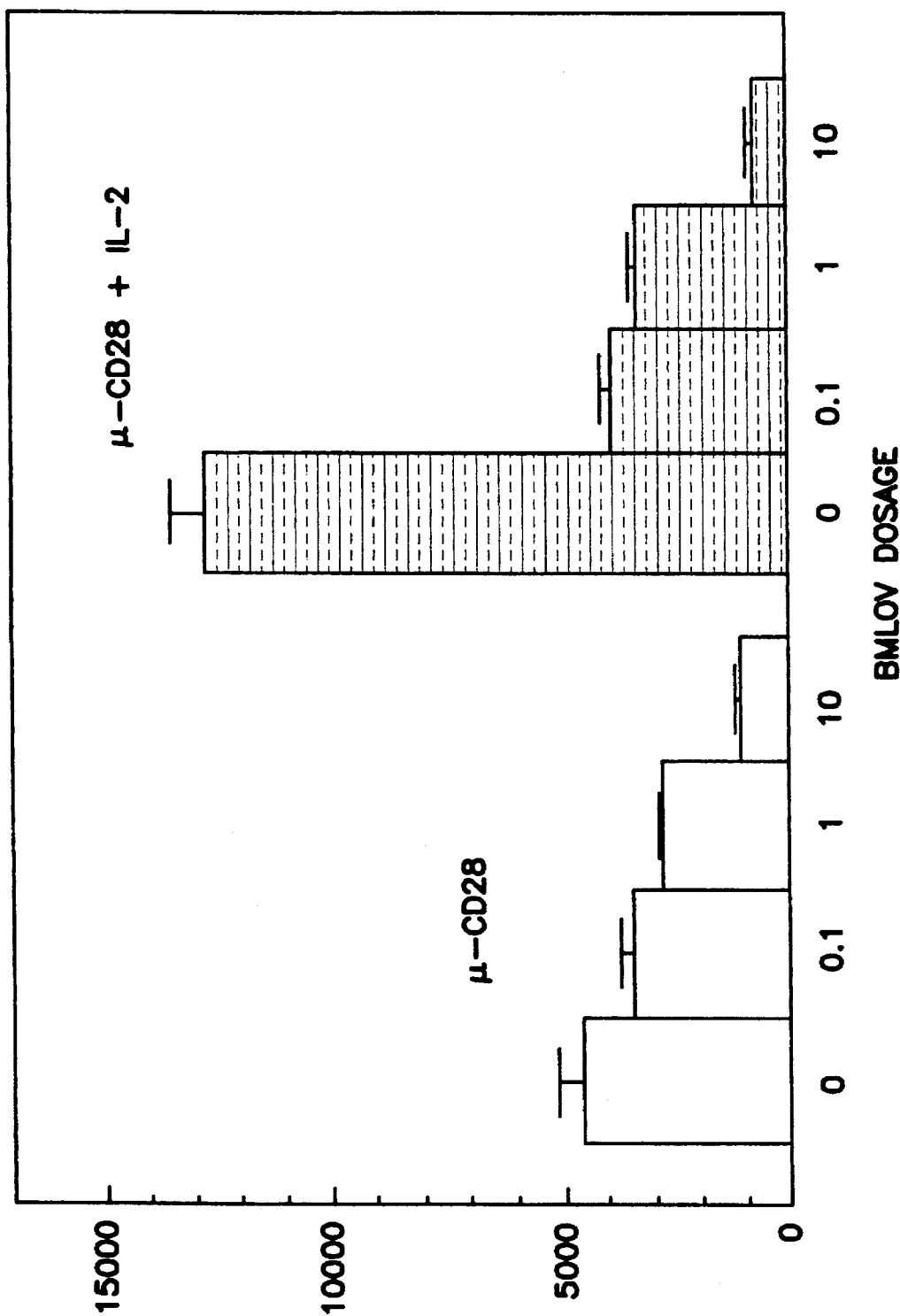
FIG. 6 is a graph showing the inhibition by BMLOV of growth of peripheral blood lymphocytes (PBL) driven by anti-CD28 antibody plus interleukin-2.
Figure 7:
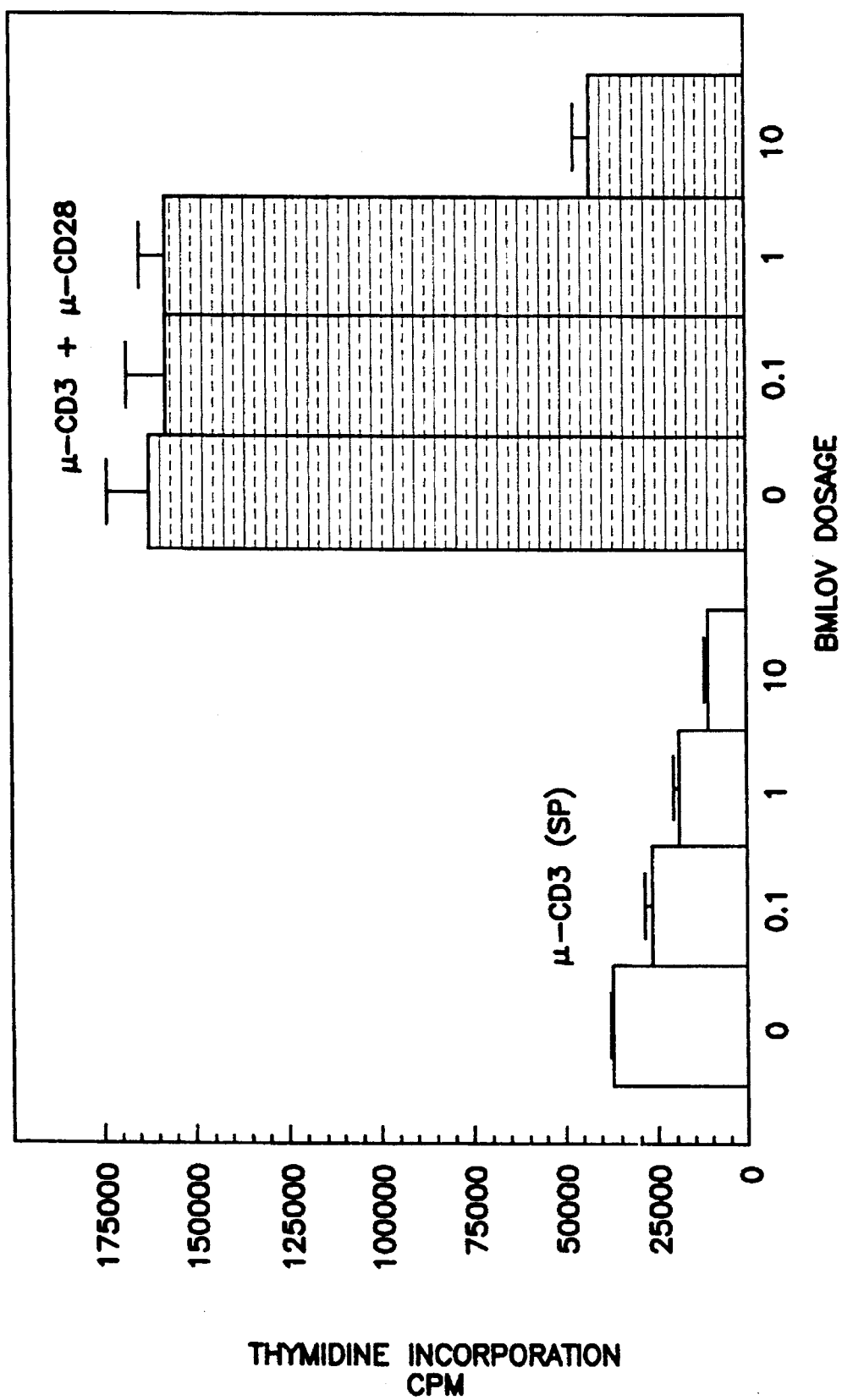
FIG. 7 is a graph showing the inhibition by BMLOV of growth of peripheral blood lymphocytes (PBL) driven by anti-CD28 antibody plus anti-CD3 antibody.

PBL growth driven by anti-CD28 antibody plus interleukin-2 (IL-2) was markedly inhibited by 1 μM BMLOV (FIG. 6) and growth driven by anti-CD3 antibody plus anti-CD28 antibody was strongly inhibited by 10 μM BMLOV (FIG. 7).

In contrast, substantially less inhibition was observed for IL-2 alone, PMA in combination with anti-CD28, or the factor-independent growth of the T cell line CEM, indicating the specificity of these effects.

Figure 8:
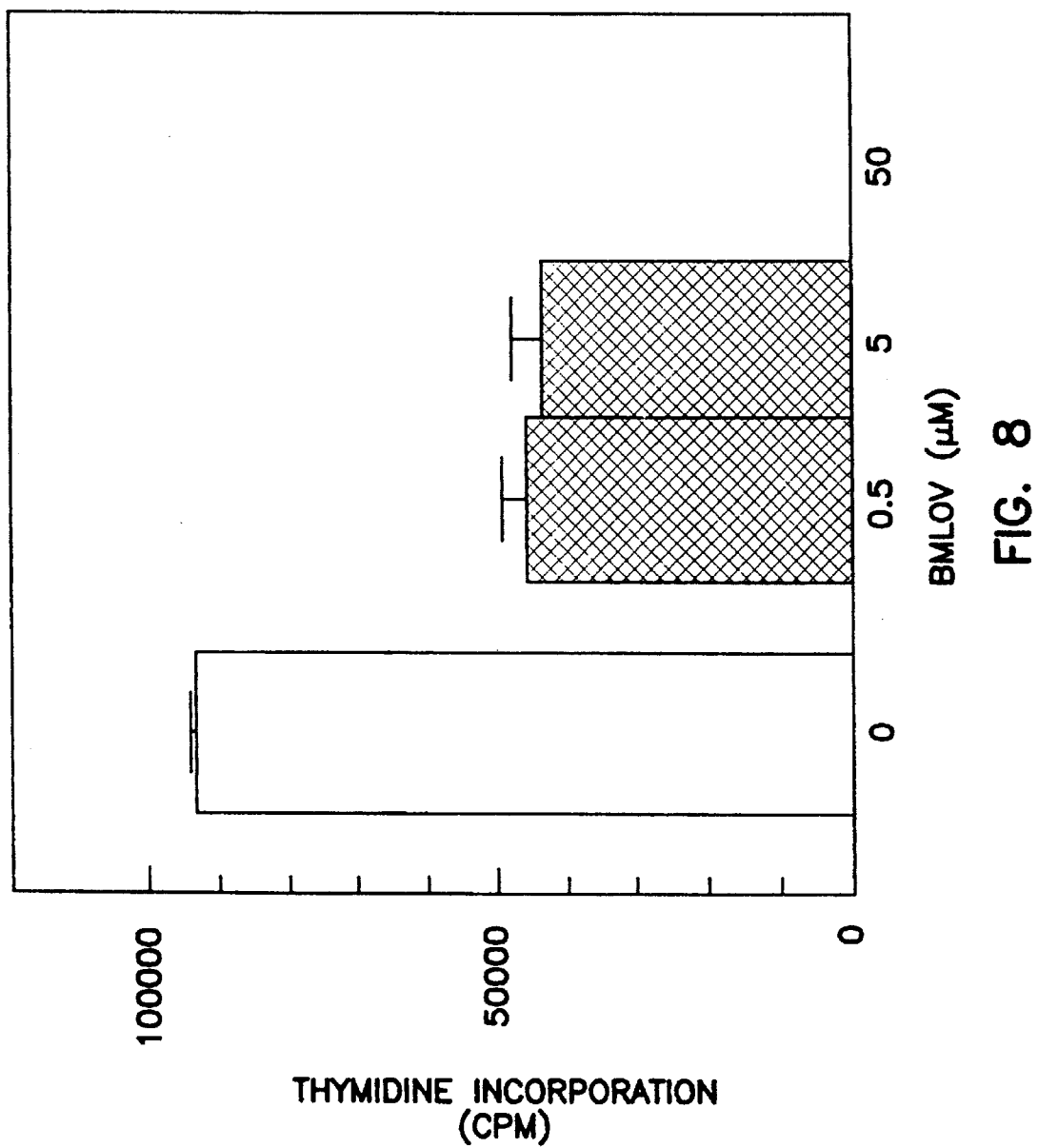
FIG. 8 is a graph showing the inhibition by BMLOV of growth in mixed lymphocyte response cultures dependent on CD28 costimulation.

Mixed lymphocyte response cultures that are dependent on CD28 costimulation were inhibited by over 50% by 0.5 to 5 μM BMLOV (FIG. 8). These results suggest the phosphatase inhibitor may selectively block CD28 effects and therefore can be used to block the generation of antibodies to antigens in animals.

An important question has been how does the costimulatory CD28 signal differ from the primary CD3 dependent signal in T cells, since both signals induce tyrosine phosphorylation and $Ca^{2+}$ flux. These results raise the possibility that the CD28 costimulatory or second signal requires a BMLOV-sensitive phosphatase activity that the primary signals do not.

Example 9

Augmentation of Signals in T and B Cells by BMLOV

BMLOV was found to markedly enhance basal calcium levels in PHA blasts when the cells were treated with doses of 50 to 100 μM for fifteen hours. These results indicate that phosphatase activity is required to maintain normal calcium levels in the cell. Treatment of the cells with 25–50 μM BMLOV was found to prolong $Ca^{2+}$ signals generated by crosslinking CD3 alone or in combination with CD2 and CD4. BMLOV greatly increased and prolonged UV-induced $Ca^{2+}$ signals in Ramos B cells, indicating that phosphatase activity may limit UV-induced signals. In contrast, BMLOV did not alter $Ca^{2+}$ signals induced in Ramos B cells by crosslinking sIg. However, BMLOV enhanced the tyrosine phosphorylation response of Ramos B cells to sIg crosslinking, particularly at early time points. These results suggest a potential for BMLOV to augment some cell responses.

Example 10

BMLOV Inhibits Src-Family Kinase Activity in Lymphocytes and Colon Carcinoma Cells The Src-family kinases are known to require cellular phosphotyrosine phosphatase activity in order for them to respond in biologically stimulated cells. This is because Src-family kinases require a C-terminal tyrosine phosphorylation site to be dephosphorylated for activation to occur. Phosphotyrosine phosphatase inhibitors may therefore be expected to inhibit Src kinases indirectly by preventing their activation.

Treatment of Ramos cells with BMLOV for 15 hours inhibited the activity of the Src kinases Lyn and Fyn from the cells by approximately 50%.

Figure 9:
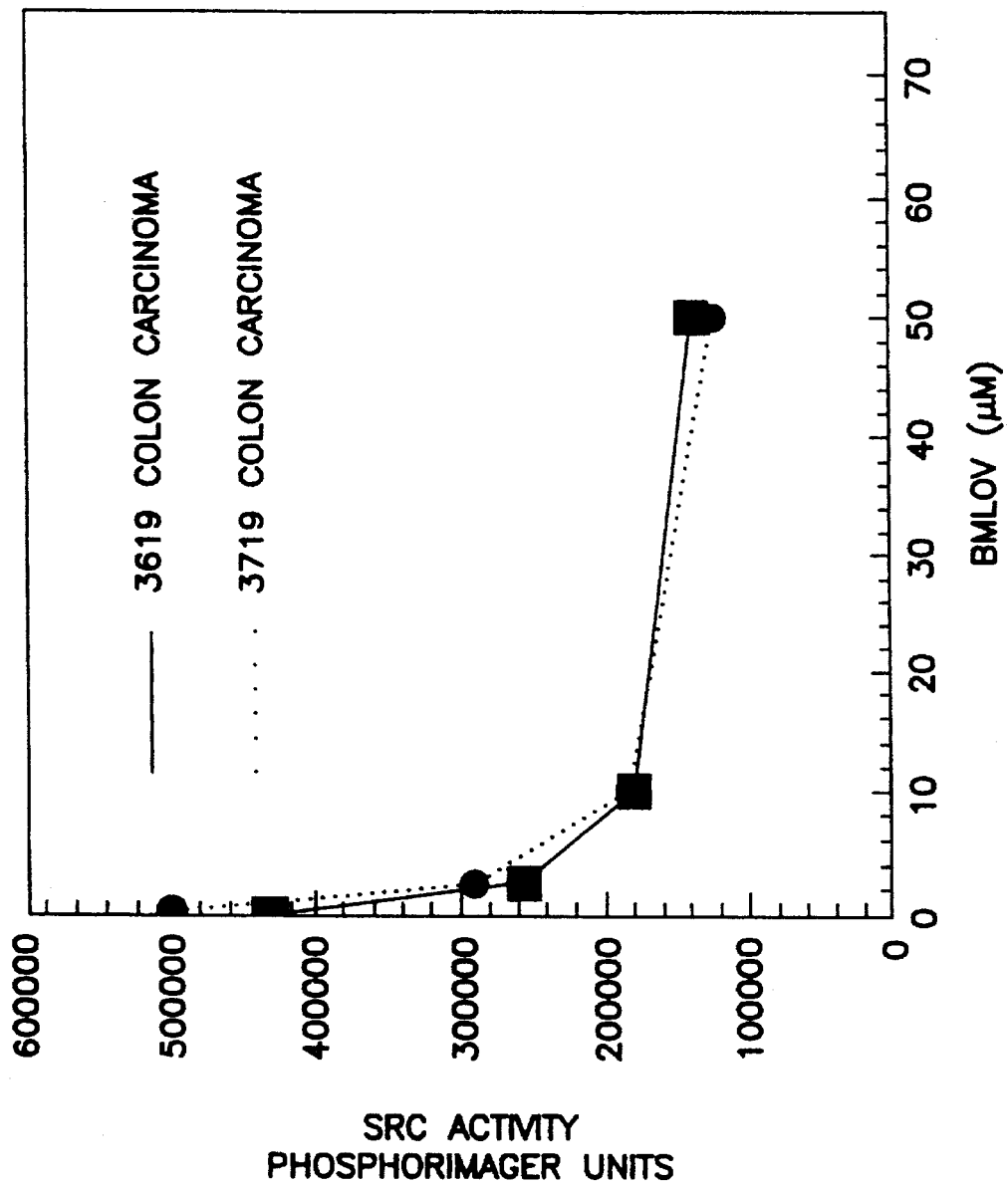
FIG. 9 is a graph showing the inhibition of $pp60^{c-src}$ kinase activity in two colon carcinoma cell lines expressing Src by BMLOV.

Many colon carcinomas are known to express the Src oncogene product at high levels. In two colon carcinoma cell lines expressing Src, $pp60^{c\text{-}src}$ activity was strongly inhibited by BMLOV in a dose-dependent fashion (FIG. 9), while $pp60^{src}$ protein level remained constant. The treated cells showed morphological changes, including decreased adherence.

Example 11

BMLOV Alters the Cell Cycle Progression of Treated Cells

A variety of anti-cancer therapies are known to alter the cell cycle progression of tumor cells. For example, both cisplatin and radiation therapy result in accumulation of cells in G2/M phase.

Ramos B cells treated with various concentrations of BMLOV for 16 hours were examined for their DNA content by propidium diiodide staining followed by FACS can flow cytometric analysis using the SFIT program.

Figure 10:
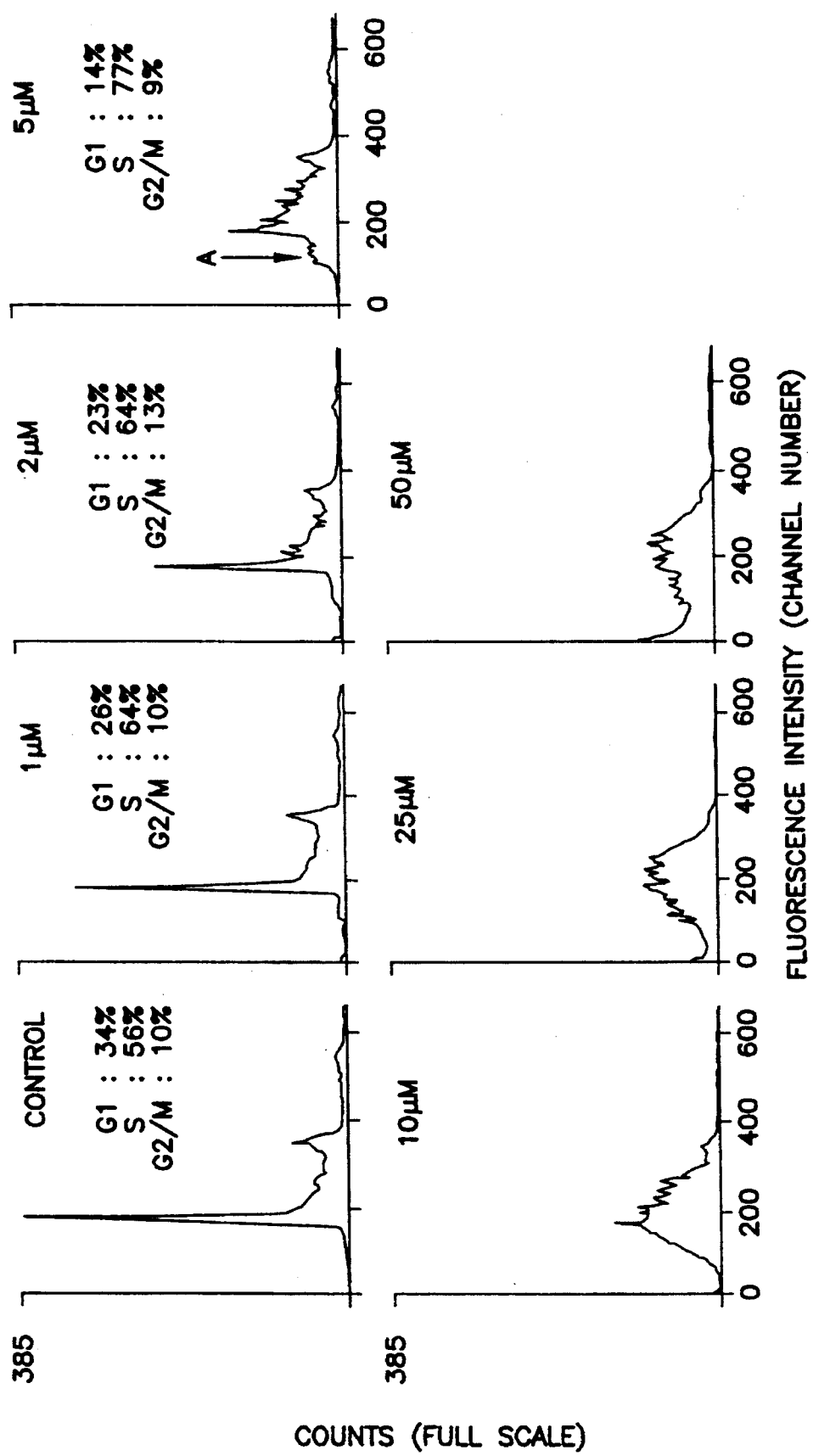
FIG. 10 is a graph showing the results of fluorescence-activated cell sorting (FACS) analysis of the cell cycle stage of Ramos B cells after treatment with BMLOV.

The results are shown in FIG. 10. The percentages of cells in G1, S, and G2/M are listed for doses of 0 to 5 µM of BMLOV. Percentages could not be calculated for higher doses due to the strong effects of the drug in causing apoptosis. Apoptotic cells lacking normal amounts of DNA are marked "A" in the 5 µM dose panel. BMLOV was found to preferentially deplete the proportion of cells in G1 while increasing the proportion in S phase. Loss of DNA due to apoptotic cell death was readily apparent in a dose of 5 µM and was greatly increased at high doses.

Example 12

Effects of Analogs of BMLOV

Two analogs of BMLOV were prepared, vanadyl 1-benzoyl acetonate and vanadyl 2-acetyl 1-tetralonate.

The synthesis of vanadyl 2-acetyl 1-tetralonate was as follows. A quantity of 2-acetyl 1-tetralone (1.13 g; 0.006 moles) was dissolved in 74 ml of water with the pH adjusted to 13 with NaOH. A small amount of insoluble material was removed. Vanadyl sulfate (0.003 moles) was then added. The solution was then heated and allowed to reflux for 1 hour. The solution was then cooled on ice and 0.884 g product (a green solid) was collected and dried over $P_2O_5$. The yield was 33%. A similar procedure was used to synthesize vanadyl 1-benzoyl acetonate, starting with 1-benzoyl acetone. Vanadyl acetylacetonate, available commercially, was also studied.

Figure 11:
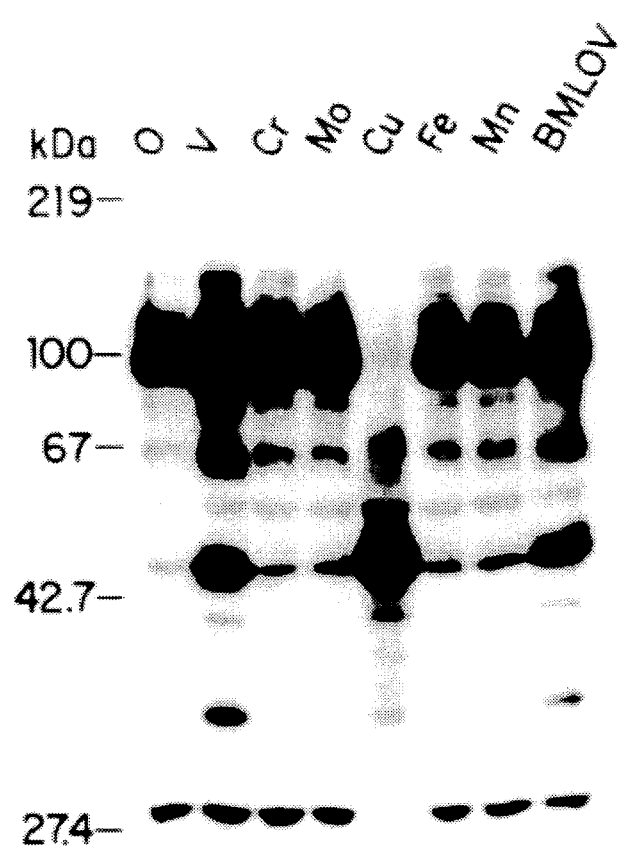
FIG. 11 is a photograph of an anti-phosphotyrosine western blot similar to those in FIGS. 1A–1C showing the effects of treating the cells with vanadyl acetylacetonate and analogs of vanadyl acetylacetonate in which the vanadium is replaced by molybdenum, chromium, iron, manganese, or copper, showing the induction of phosphorylation by vanadyl acetylacetonate in a pattern similar to that of BMLOV.

Of these analogs, only vanadyl acetylacetonate and vanadyl 1-benzoyl acetonate strongly induced cellular tyrosine phosphorylation. As shown in FIG. 11, anti-phosphotyrosine western blot analysis of whole cell lysates following SDS-PAGE revealed that vanadyl acetylacetonate strongly induced tyrosine phosphorylation in a pattern very similar to that of BMLOV.

Analogs of vanadyl acetylacetonate were prepared in which the vanadium was replaced with other metals, namely molybdenum, chromium, iron, manganese, or copper. Of these analogs with differing metal ions, only cupric acetylacetonate induced tyrosine phosphorylation, but in a different pattern than for the vanadyl compounds (FIG. 11). Thus, only certain metals are active in this type of compound.

Clonogenic assays of Ramos Burkitt lymphoma cells treated with cupric acetylacetonate showed that the cells were sensitive to the compound at doses of 10 and 25 µM (Table 5).

TABLE 5

Effect of Cupric Acetylacetonate on Ramos B Cells as Measured in Clonogenic Assays

| Dose, µM | Colonies | SE |
|---|---|---|
| 0 | 9126 | 1944 |
| 1 | 5749 | 1070 |
| 5 | 226 | 26 |
| 10 | 127 | 35 |
| 25 | 31 | 8 |

Example 13

BMLOV Was Tolerated by Animals

BMLOV is tolerated by animals when it was administered by oral or intraperitoneal routes. Mice were treated with 1.6 mM of BMLOV in their drinking water continuously for 10 days, and the level of the drug in their blood serum was determined by atomic absorption spectroscopy after 1 and 10 days of treatment, as shown in Table 6. The mice displayed no overt ill effects from the drug treatment. Subsequently, mice have received intraperitoneal doses of BMLOV of up to 1 mg and oral doses of up to 1.6 mg without ill effects except for some temporary lethargy.

TABLE 6

BMLOV Levels in Mouse Sera

| Mouse | Day | BMLOV in Serum, µM |
|---|---|---|
| 647 | 1 | 9.5 |
| 648 | 1 | 5.3 |
| 649 | 1 | 7.5 |
| 650 | 1 | 8.7 |
| 647 | 10 | 11.4 |
| 648 | 10 | 11.0 |
| 649 | 10 | 7.5 |
| 650 | 10 | 7.7 |

Example 14

Prevention of Class-Switching in Antibody-Producing B Cells by BMLOV

The effects of BMLOV were assayed on class-switching in antibody-producing B cells. Human B cells producing antibody were treated with anti-CD40 antibody plus IL-4, which increased production of IgE over 10-fold (Table 7). However, in the presence of 5.6 or 17 µM BMLOV, the increased production of IgE was markedly inhibited. In contrast, the production of IgG1 and IgG4 was much less affected, particularly at a dose of 5.6 µM BMLOV. This selective effect is important because the IgG antibody production is an important response to infectious disease. It would be of value to suppress IgE production for the treatment of allergies while maintaining IgG production, particularly in conditions in which an allergy coexists with an infectious disease. A common example is the exacerbation of allergic rhinitis (hay fever) as the result of a respiratory infection.

TABLE 7

EFFECT OF BMLOV N CLASS-SWITCHING IN ANTIBODY-PRODUCING B CELLS

| Treatment of Cells | [Ig], ng/ml: | | | |
|---|---|---|---|---|
| | IgG1 | Ig64 | IgM | IgE |
| Untreated | 225 | 0.7 | 6.6 | 0.5 |
| Anti-CD40 + IL-4 | 510 | 1.7 | 16.8 | 5.7 |
| Anti-CD40 + IL-4 + 0.002 μM BMLOV | 450 | 1.7 | 20.4 | 3.9 |
| Anti-CD40 + IL-4 + 0.008 μM BMLOV | 450 | 1.1 | 20.4 | 2.6 |
| Anti-CD40 + IL-4 + 0.02 μM BMLOV | 390 | 1.3 | 19.2 | 4.5 |
| Anti-CD40 + IL-4 + 0.07 μM BMLOV | 450 | 2.7 | 12.0 | 5.1 |
| Anti-CD40 + IL-4 + 0.2 μM BMLOV | 495 | 1.2 | 13.8 | 7.5 |
| Anti-CD40 + IL-4 + 0.6 μM BMLOV | 480 | 1.3 | 17.4 | 5.7 |
| Anti-CD40 + IL-4 + 1.9 μM BMLOV | 450 | 2.7 | 15.6 | 3.0 |
| Anti-CD40 + IL-4 + 5.6 μM BMLOV | 480 | 1.8 | 18.6 | 1.2 |
| Anti-CD40 + IL-4 + 17 μM BMLOV | 450 | 0.8 | 18.0 | 0.8 |
| IL-4 + 50 μM BMLOV | 60 | 0.5 | 5.1 | 0.2 |

ADVANTAGES OF THE INVENTION

The present invention provides methods for inhibiting phosphotyrosine phosphatase, particularly in B cells. This yields improved methods of inhibiting the proliferation of these cells by exploiting the occurrence of apoptosis (programmed cell death). These methods can be exploited for treatment of disorders marked by malignant proliferation of B cells, such as leukemias and lymphomas, and can be combined with other methods of treatment, including radiation. Such a combination yields synergistic effects over either radiation alone or the use of phosphotyrosine phosphatase inhibitors alone.

Methods according to the present invention can also be used for controlling proliferation of non-malignant B cells for regulation of the immune response. This is desirable for the treatment of autoimmune disease and for controlling transplant rejection, as well as for controlling class-switching in antibody-producing cells.

The methods of the present invention are further useful for studying signaling in B cells and for screening for abnormalities of B cell signaling.

Although the present invention has been described with considerable detail, with reference to certain preferred versions thereof, other versions are possible. Therefore, the spirit and scope of the appended claims should not be limited to the description of the preferred versions contained herein.

I claim:

1. Vanadyl 2-acetyl-1-tetralone.

2. Vanadyl 2-hydroxy-4-isopropyl-2,4,6-cycloheptatrien-1-one.

3. Vanadyl 2-hydroxy-4-methyl-2,4,6-cycloheptatrien-1-one.

4. A metal-organic covalent compound comprising vanadium (IV) coordinate-covalently bound to an organic moiety that is a keto-enol tautomer with the keto and enol groups on adjacent carbon atoms and that forms a 5-membered ring including the metal, the organic moiety being selected from the group consisting of 2-hydroxy-2,4,6-cycloheptatrien-1-one, 3-bromo-2-hydroxy-2,4,6-cycloheptatrien-1-one, 3-hydroxy-1,2-dimethyl-4(1H)-pyridone, 3-ethyl-2-hydroxy-2-cyclopenten-1-one, 3,4-dihydroxy-3-cyclobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione, 2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, alpha-acetyl-4-hydroxy-beta-(hydroxymethyl)-3-methoxycinnamic acid gamma-lactone, 4-hydroxy-5-phenyl-4-cyclopenten-1,3-dione, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 1,2,7-trihydroxyanthraquinone, fisetin, 3-oxo-4,5,6-trihydroxy-3(H)-xanthene-9-propionic acid, benzoin, 4'-chlorobenzoin, quercetin, morin, myricetin, and 4,4'-dimethylbenzoin.

5. A metal-organic covalent compound comprising vanadium (IV) coordinate-covalently bound to an organic moiety that is a beta diketone in which the two keto groups are separated by one carbon atom that forms a 6-membered ring including the metal, the organic moiety being selected from the group consisting of 2-acetyl-1-tetralone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thenoyltrifluoroacetone, S-t-butylacetothioacetate, 3-acetyl-5-methylhexan-2-one, 3-acetyl-2-heptanone, 2,2-dimethyl-6,6,7,7,8,8,8-heptafluoro-3,5-octanedione, 4-hydroxy-5-phenyl-4-cyclopenten-1,3-dione, 4,4,4-trifluoro-1-phenyl-1,3-butanedione, 3-acetyl-2-octanone, 1(2-hydroxy-4-methylphenyl)-1,3-butanedione, 1-(2-hydroxy-5-methylphenyl)-1,3-butanedione, 3-benzylidene-2,4-pentanedione, 1-(2-hydroxy-5-methylphenyl)-1,3-pentanedione, 2,2,6,6-tetramethyl-3,5-heptanedione, 3-acetyl-5-hydroxy-2-methylchromone, (+)-3-(trifluoroacetyl)camphor, 4,9-dihydro-6-methyl-5H-furo(3,2-g)(1) benzopyran-4,5,9-trione, 3-(2-nitrobenzylidene)-2,4-pentanedione, 1,3-bis(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione, 2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl)methane, and curcumin.

* * * * *

UNITED STATES PATENT AND TRADEMARK OFFICE
CERTIFICATE OF CORRECTION

PATENT NO. : 5,583,242

DATED : December 10, 1996

INVENTOR(S) : Schieven

It is certified that error appears in the above-identified patent and that said Letters Patent is hereby corrected as shown below:

Column 7, line 7, delete ",cycloheptatrien-1-one" after the word "cycloheptatrien-1-one"

Column 8, line 20, "electropherogramon" should read --electropherogram on--

Column 8, line 49, "pp60$^{c-src}$" should read --pp60$^{c-Src}$--

Column 27, line 3, "pp60$^{c-src}$" should read --pp60$^{c-Src}$--

Column 12, line 66, "(CH$_2$-)a" should read --(CH$_2$-)$_2$--

Column 14, line 38, "C$_{1-c5}$" should read --C$_1$-C$_5$--

Column 14, line 39, "C$_1$-$^S$5" should read --C$_1$-C$_5$--

Column 17, line 49, "Judged" should read --judged--

UNITED STATES PATENT AND TRADEMARK OFFICE
CERTIFICATE OF CORRECTION

PATENT NO. : 5,583,242

DATED : December 10, 1996

INVENTOR(S) : Schieven

It is certified that error appears in the above-identified patent and that said Letters Patent is hereby corrected as shown below:

Column 18, line 27, "Judgement" should read --judgement--

Column 22, lines 20 & 25, "RaJi" should read --Raji--

Column 27, line 5, "pp60$^{src}$" should read --pp60$^{c-src}$--

Column 27, line 64, delete "." after the word "induced"

Column 29, Tbl 7, line 2, "N" should read --ON--

Signed and Sealed this

Fifth Day of August, 1997

*Attest:*

*Attesting Officer*

BRUCE LEHMAN

*Commissioner of Patents and Trademarks*